(12) United States Patent
Weissman et al.

(10) Patent No.: US 12,370,243 B2
(45) Date of Patent: Jul. 29, 2025

(54) NON-GENOTOXIC CONDITIONING REGIMEN FOR STEM CELL TRANSPLANTATION

(71) Applicant: The Board of Trustees of the Leland Stanford Junior University, Stanford, CA (US)

(72) Inventors: Irving L. Weissman, Stanford, CA (US); Judith A. Shizuru, Palo Alto, CA (US); Akanksha Chhabra, San Francisco, CA (US); Benson M. George, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 960 days.

(21) Appl. No.: 17/185,386

(22) Filed: Feb. 25, 2021

(65) Prior Publication Data

US 2021/0177949 A1    Jun. 17, 2021

Related U.S. Application Data

(62) Division of application No. 15/884,017, filed on Jan. 30, 2018, now abandoned.

(60) Provisional application No. 62/452,218, filed on Jan. 30, 2017.

(51) Int. Cl.
| | | |
|---|---|---|
| A61K 39/00 | (2006.01) |
| A61K 35/28 | (2015.01) |
| A61K 39/395 | (2006.01) |
| A61P 37/06 | (2006.01) |
| C07K 16/28 | (2006.01) |
| A61K 35/12 | (2015.01) |

(52) U.S. Cl.
CPC ...... *A61K 39/001* (2013.01); *A61K 39/39541* (2013.01); *A61P 37/06* (2018.01); *C07K 16/2803* (2013.01); *C07K 16/2866* (2013.01); *C07K 16/2875* (2013.01); *A61K 2035/122* (2013.01); *A61K 2039/505* (2013.01)

(58) Field of Classification Search
None
See application file for complete search history.

(56) References Cited

U.S. PATENT DOCUMENTS

| | | |
|---|---|---|
| 5,877,299 A | 3/1999 | Thomas |
| 10,406,179 B2 | 9/2019 | Shizuru |
| 2005/0112122 A1 | 5/2005 | Greiner |
| 2006/0147428 A1 | 7/2006 | Sachs |
| 2013/0189253 A1 | 7/2013 | Danska |
| 2017/0151327 A1 | 6/2017 | Lui |
| 2019/0134217 A1 | 5/2019 | Nixon |

FOREIGN PATENT DOCUMENTS

| | | |
|---|---|---|
| WO | WO2003054019 | 7/2003 |
| WO | WO2004002425 | 1/2004 |
| WO | WO2005/021734 | 3/2005 |
| WO | WO2008067115 | 6/2008 |
| WO | WO2016033201 | 3/2016 |
| WO | WO2016094679 | 6/2016 |
| WO | WO2016154588 | 9/2016 |
| WO | WO2016164502 | 10/2016 |

OTHER PUBLICATIONS

Bartolovic et al., "Inhibitory effect of imatinib on normal progenitor cells in vitro" Blood, Jan. 15, 2004, pp. 523-529, vol. 103, No. 2, The American Society of Hematology, Washington, D.C.

Burt et al., "Treatment of autoimmune disease by intense immunosuppressive conditioning and autologous hematopoietic stem cell transplantation", Blood, Nov. 15, 1998, pp. 3505-3514, vol. 92(10), The American Society of Hematology, Washington, D.C.

Chen et al., "Bystander destruction of hematopoietic progenitor and stem cells in a mouse model of infusion-induced bone marrow failure", Blood, Sep. 15, 2004, pp. 1671-1678, 104(6), The American Society of Hematology, Washington, D.C.

Chhabra et al. (2014) "Successful Engraftment of Hematopoietic Stem Cells into Immunocompetent Recipients Using Only Anti-CD117 Antibody and CD47 Blockade as Conditioning" Blood, 2014,v.124, p. 2410.

Chhabra et al., "Hematopoietic stem cell transplantation in immunocompetent hosts without radiation or chemotherapy," Sci Transl Med, Aug. 10, 2016, pp. 1-11, vol. 8, No. 35, American Association for the Advancement of Science, Washington, D.C.

Czechowicz et al., "Efficient transplantation via antibody-based clearance of hematopoietic stem cell niches." Science, Nov. 23, 2007, pp. 1296-1299, vol. 318, No. 5854, AAAS, Washington, DC.

Gaspar et al., "Successful Reconstitution of Immunity in ADA-SCID by tem Cell Gene Therapy Following Cessation of PEG-ADA and Use of Mild Preconditioning", Molecular Therapy, Oct. 2006, pp. 505-513, vol. 14(4), The American Society of Gene Therapy, Milwaukee, WI.

Ishikawa et al., "An assay for long-term engrafting human hemopoietic cells based on newborn NOD/SCID Beta 2-microglobulin(null) mice", Experimental Hematology, Jan. 22, 2002, pp. 488-494, 30(5), Elsevier, Amsterdam, Netherlands.

Jacobsohn et al., "Reduced intensity haemopoietic stem-cell transplantation for treatment of non-malignant diseases in children", The Lancet, Jul. 10, 2004, pp. 156-162, 364(9429), The Lancet, London, United Kingdom.

(Continued)

*Primary Examiner* — Michail A Belyavskyi

(74) *Attorney, Agent, or Firm* — Pamela J. Sherwood; Bozicevic, Field & Francis LLP

(57) ABSTRACT

The present invention provides a clinically applicable method of stem cell transplantation that facilitates engraftment and reconstitutes immunocompetence of the recipient without requiring radiotherapy or chemotherapy, and without development of GVHD or graft rejection.

10 Claims, 27 Drawing Sheets

(56) References Cited

OTHER PUBLICATIONS

Kim et al (2003) "Successful allogenic hematopoietic stem cell transplantation using triple agent immunosuppression in serve aplastic anemia patients" Bone Marrow Transplantation, v.31, pp. 79-86.
Kraft et al. "Ability of Anti C-knit Targeting Monoclonal Antibody ACK-2 To Target hematopoietic stem cells and Facilitate Engraftment of human CD34+ Engraftment and Hematolymphoid Development in Immunodeficient Mice: A novel Antibody based Conditioning strategy" (2007), Biology of Blood and Marrow,v.13,N.2,p. 72.
Kraft et al., "Effect and kinetics of depleting ACK-2 anti c-kit monoclonal antibody on hematopoiesis and hematopoietic progenitors and ability to condition for bone marrow transplantation" Blood, (Ash Annual Meeting Abstracts), Nov. 1, 2004, p. 322B, vol. 104, No. 11, Abstract 4963, The American Society of Hematology, Washington, D.C.
Kraft et al., "196—Ability Of Anti C-Kit Targeting Monoclonal Antibody Ack-2 To Target Hematopoietic Stem Cells, And Facilitate Engraftment Of Human CD34+ Engraftment And Hematolymphoid Development In Immunodeficient Mice: A Novel Antibody Based Conditioning Strategy", Biology of Blood and Marrow Transplantation (2007), Poster Session I, 13(2):72, Elsevier, Amsterdam, Netherlands.

Kraft et al., "378—Adult human hematopoietic cells differentiate into mature T cells via a CD3-4+8-intermediate within the mouse thymic microenvironment; a new model system for the study of human thymocyte development further enhanced by anti-murine c-Kit mAB", Biology of Blood and Marrow Transplantation, Feb. 1, 2006, Poster Session II, p. 131, vol. 12, No. 2, Carden Jennings Publishing Co, Charlottesville, VA.
Murray et al. {2002) "Non-Cancer Therapeutic Anti Bodies" Expert Opinion On Therapeutic Patents, vo 1, 12. no. 3. pp. 401-417.
Partridge et al. "Enhanced Engraftment of Hematopoietic Stem Cells (HSCs) by Inhibition of Mammalian Target of Rapamycin" (2013) Molecular Therapy,v.21, Suppl S160-S161.
Quesenberry et al., "Stem cell homing: Rolling, crawling, and nesting", PNAS, Dec. 1998, pp. 15155-15157 vol. 95, National Academy of Sciences, Washington, D.C.
Remberger et al. {1999) "Effect on cytokine release and graft-versus-host disease of different anti-T cell antibodies uring conditioning for unrelated hematopoietic stem cell transplantation" Bone Marrow Transplantation, vol. 24. No. 8. pp. 823-830.
Xue et al., "Antibody targeting KIT as pre-transplantation conditioning in immunocompetent mice," Blood, Sep. 2, 2010, pp. 5419-5422, vol. 116(24), The American Society of Hematology, Washington, D.C.
Duncan et al. (2005) "Transplant-related immunosuppression: a review of immunosuppression and pulmonary infections". Proc Am Thorac Soc. :2(5):449-455.

AKR x Hz (F1);
CD45.1/CD45.2;
H2Kk/H2Kb

30e6
WBM

Balb/c x C57BL/6 (F1);
CD45.2;
H2Kd/H2Kb

Days:  -8  -7  -6  -5  -4  -3  -2  -1  0

CD47(Clone 3)  X      X   X   X   X   X
c-KIT (ACK2)           X
CD122 (Tm-b1)                          X
CD40L (MR-1)                               X
Transplant                                 X

FIG. 2

| Conditioning Regimen | % of Chimeric Mice | % Total Donor Chimerism | % Donor T-Cell Chimerism | % Donor B-Cell Chimerism | % Donor Granulocyte Chimerism |
|---|---|---|---|---|---|
| PBS | 0 (0/2) | 0.07 | 0.00 | 0.13 | 0.00 |
| CD122 | 0 (0/3) | 0.08 | 0.02 | 0.14 | 0.07 |
| MR1 | 0 (0/3) | 0.10 | 0.04 | 0.16 | 0.04 |
| ACK2 | 0 (0/3) | 0.09 | 0.07 | 0.14 | 0.00 |
| Clone3 | 0 (0/2) | 0.08 | 0.09 | 0.18 | 0.00 |
| ACK2 + Clone3 | 0 (0/3) | 0.08 | 0.03 | 0.14 | 0.04 |
| ACK2 + Clone3 + MR1 | 75 (3/4) | 53.47 | 59.93 | 46.10 | 72.83 |
| ACK2 + Clone3 + CD122 | 0 (0/3) | 0.06 | 0.03 | 0.09 | 0.11 |
| ACK2 + Clone3 + MR1 + CD122 | 100 (4/4) | 50.43 | 52.63 | 44.05 | 71.50 |

AKR x Hz (F1);
CD45.1/CD45.2;
H2Kk/H2Kb

Balb/c x C57BL/6 (F1);
CD45.2;
H2Kd/H2Kb

| Days: | -8 | -7 | -6 | -5 | -4 | -3 | -2 | -1 | 0 |
|---|---|---|---|---|---|---|---|---|---|
| CD47(Clone 3) | X | | X | X | X | X | X | | |
| c-KIT (ACK2) | | | X | | | | | | |
| CD122 (Tm-b1) | | | | | | | X | | |
| CD40L (MR-1) | | | | | | | | | X |
| Transplant | | | | | | | | | X |

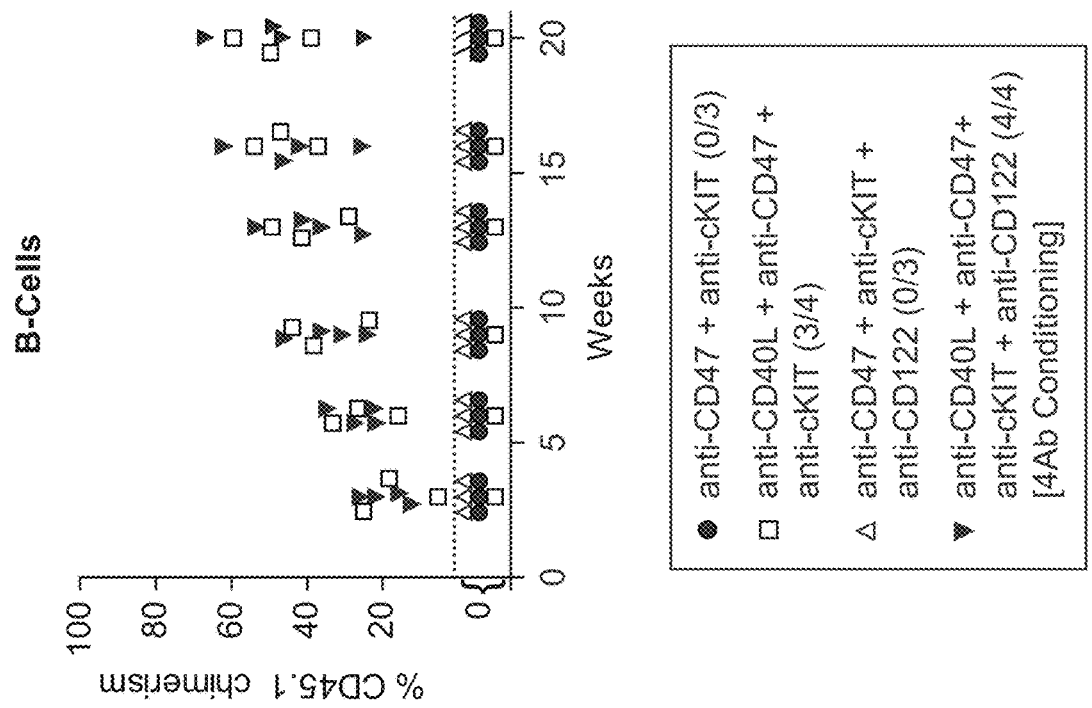
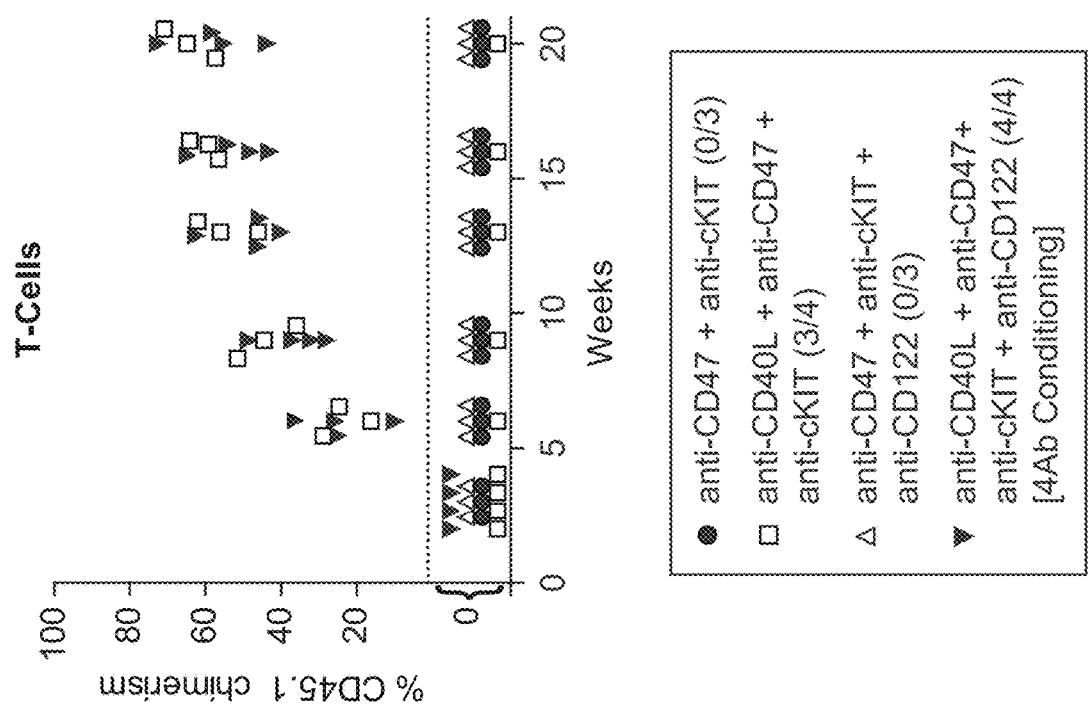

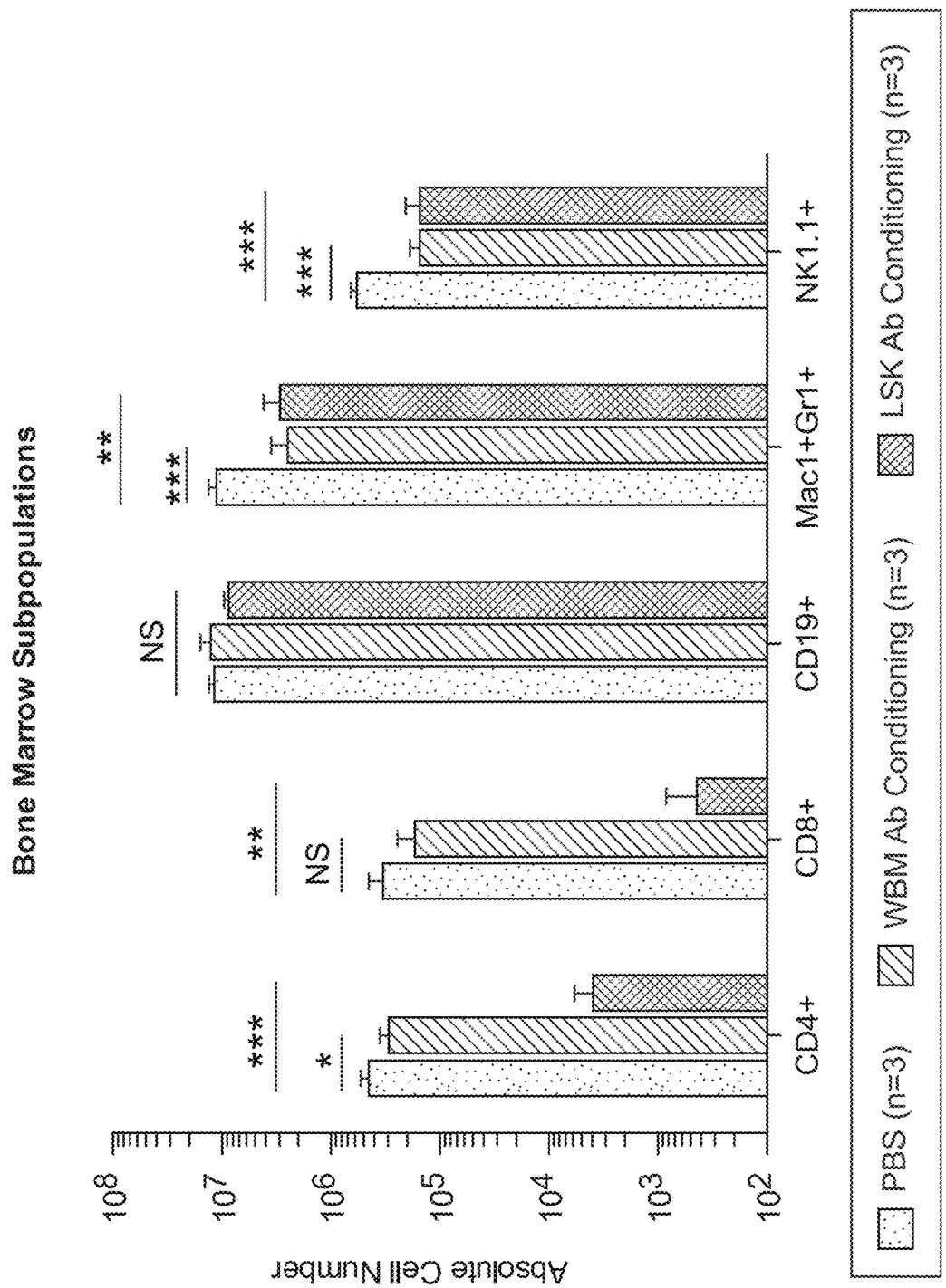

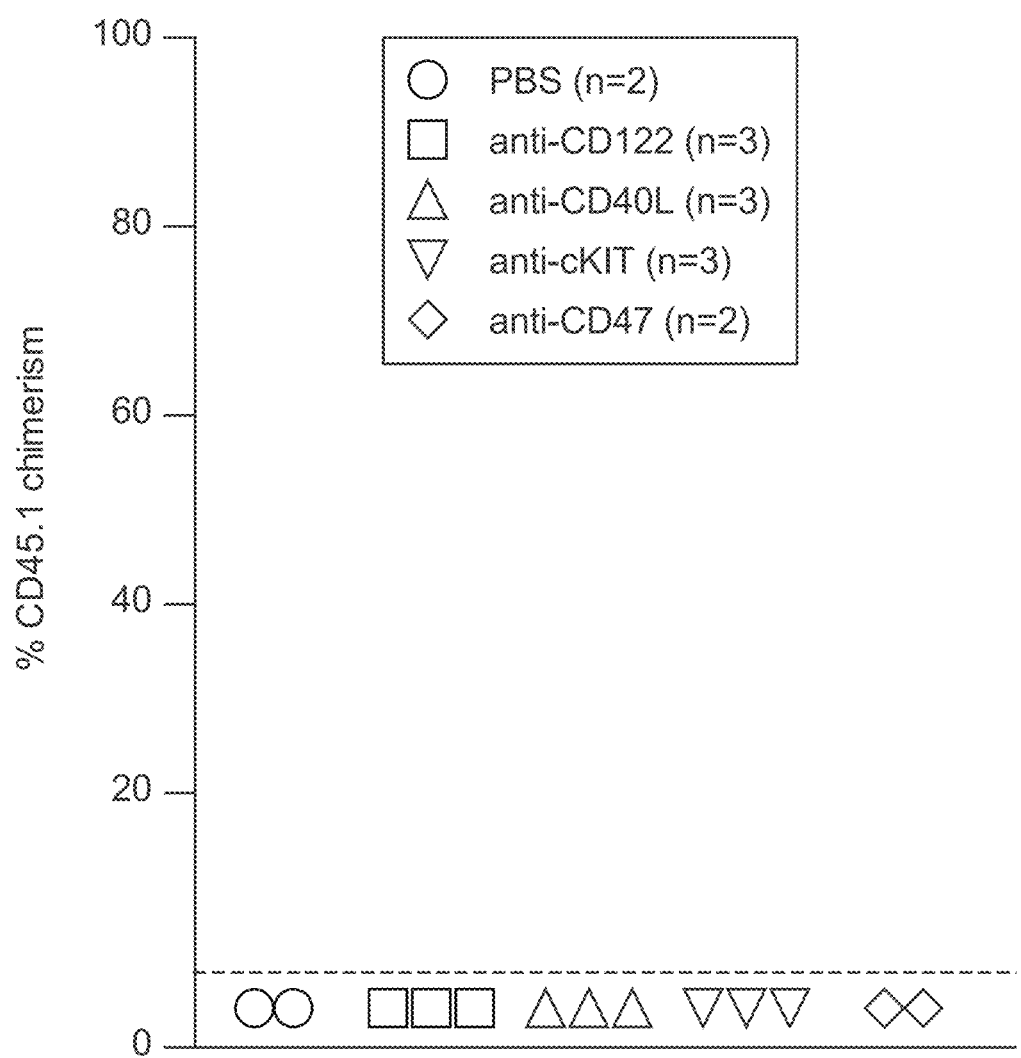

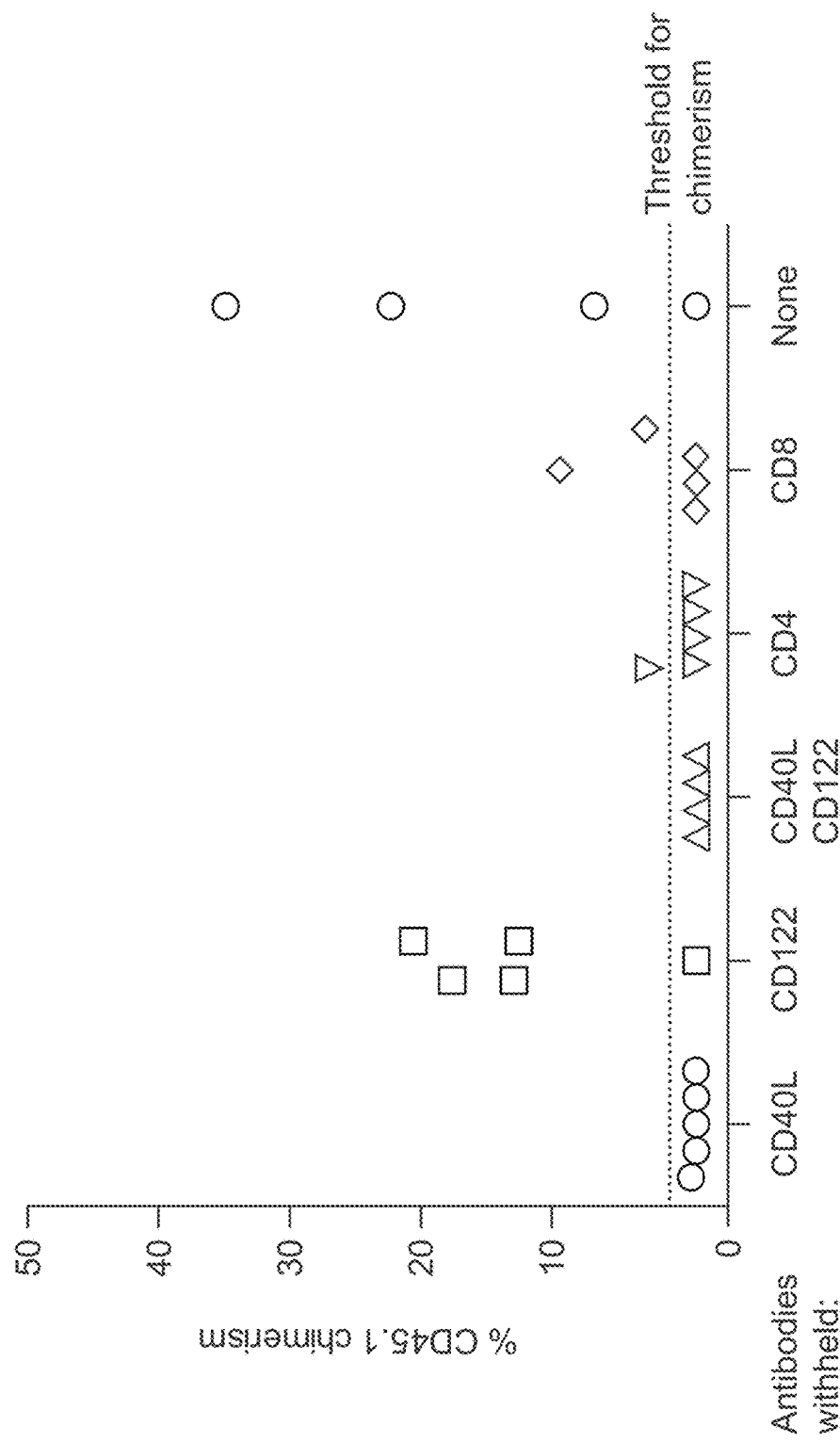

NON-GENOTOXIC CONDITIONING REGIMEN FOR STEM CELL TRANSPLANTATION

CROSS REFERENCE

This application is a Divisional and claims the benefit of U.S. patent application Ser. No. 15/884,017, filed Jan. 30, 2018, which claims the benefit of U.S. Provisional Patent Application No. 62/452,218, filed Jan. 30, 2017, which applications are incorporated herein by reference in their entirety.

Stem cells provide the means for organisms to maintain and repair certain tissues, through the ability of these cells to self-renew and to generate differentiated cells. Clinically, bone marrow and hematopoietic stem cell transplantation are widely used as a means of providing patients with the capacity to generate blood cells, usually where the patient has been depleted of endogenous stem cells by high dose chemotherapy or radiation.

Hematopoietic cell transplantation (HCT) generally involves the intravenous infusion of autologous or allogeneic blood forming cells, the active subset of which are hematopoietic stem cells (HSC); these are collected from bone marrow, peripheral blood, or umbilical cord blood and transplanted to reestablish hematopoietic function in patients whose bone marrow or immune system is damaged or defective. This procedure is often performed as part of therapy to eliminate a bone marrow infiltrative process, such as leukemia, or to correct congenital immunodeficiency disorders. In addition, HCT is used to allow patients with cancer to receive higher doses of chemotherapy than bone marrow can usually tolerate; bone marrow function is then salvaged by replacing the marrow with previously harvested stem cells. Enriched or purified populations of HSC can also be transplanted, and are not contaminated with other cells, many of which are deleterious to the host.

The preparative or conditioning regimen is a critical element in hematopoietic cell transplantation (HCT). In a successful transplantation, clearance of bone-marrow niches must be achieved for donor hematopoietic stem cell (HSC) to engraft. The preparative regimen may also provide immunosuppression sufficient to prevent rejection of the transplanted graft, and to eradicate the disease for which the transplantation is being performed. Current methods to clear niche space rely on radiation and/or chemotherapy, which can impart toxic adverse effects that greatly limit the potential clinical utility of BMT. Traditionally, myeloablative conditioning is performed.

Myeloablative regimens can be classified as radiation-containing or non-radiation-containing regimens, therapies that were developed by escalating the dose of radiation or of a particular drug to the maximally tolerated dose. Total-body irradiation and cyclophosphamide or busulfan and cyclophosphamide are the commonly used myeloablative therapies. These regimens are especially used in aggressive malignancies, such as leukemias. However, such treatment carries a number of disadvantages in terms of toxicity to the patient.

Improved methods for engraftment of stem cells, including hematopoietic stem cells, are of great clinical interest. The present invention addresses this need.

SUMMARY OF THE INVENTION

Methods and compositions are provided for the long term multilineage engraftment of stem cells, including without limitation hematopoietic stem cells, in a recipient, by: treating the recipient with a pre-transplantation non-myeloablative, non-genotoxic conditioning regimen; and administering an effective dose of a cell population comprising exogenous stem cells. The conditioning regimen comprises administration of agents that act on endogenous cell populations for various purposes. The methods allow engraftment to treat hematologic disorders, and can also be used to tolerize a recipient to a donor-type HLA for future organ transplantation.

Endogenous stem cells are depleted by the conditioning regimen. Agents that deplete endogenous stem cells include, without limitation, an antibody specific for c-kit and an agent that blockades CD47 activity. These agents are also capable of depleting the exogenous stem cells after administration, and so require a "wash-out" period from the time the agents are administered to the time the exogenous stem cells are administered. The wash-out period is sufficient to reduce the serum levels of the agents that deplete endogenous stem cells to a non-toxic level, that does not result in depletion of stem cells.

In some embodiments at least one agent is included in the conditioning regimen that provides transient immune suppression of cytotoxic lymphocytes. A variety of biological and non-myeloablative pharmaceutical agents are available for this purpose, including without limitation an agent that inhibits CD40/CD40L activity; mycophenolic acid, cyclosporine A, rapamycin, FK506, corticosteroids, etc. In some embodiments an agent inhibits CD40L, and is an antibody specific to CD40L. The transient immunosuppressive agent can be administered prior to or concomitantly with the exogenous stem cells, so long as the agent is active when the exogenous stem cells are administered.

In some embodiments at least one agent is included in the conditioning regimen that depletes one or both of T lymphocytes and natural killer (NK) cells. Agents that deplete T cells specifically include without limitation, agents, including antibodies, specific for CD3, CD4, CD8, etc. Agents that deplete T cells and NK cells include without limitation, agents, including antibodies, specific for CD2, CD52, CD45, anti-thymocyte globulin (ATG), etc. Agents that deplete NK cells specifically include without limitation, agents, including antibodies, specific for CD122, CD56, etc. The depleting agent(s) can be administered prior to infusion the exogenous stem cells, and are optionally active after infusion, so long as the targeted cells have been depleted when the exogenous stem cells are administered.

In one embodiment, methods are provided for the selection and administration of an appropriate set of agents for non-genotoxic conditioning prior to transplantation. It is shown herein that the requirements of a pre-conditioning regimen for successful engraftment of stem cells varies according to certain parameters, including the number of donor cells administered to the recipient; the purity of the donor cells; the degree of major histocompatibility mismatch between donor and recipient; and the immune status of the recipient. Selecting the appropriate set of agents for the individual, and the timing for administration of the agents, can optimize the therapeutic results of the transplantation.

In some embodiments, the methods described herein may comprise the steps of: HLA typing a donor and recipient to determine an HLA-matched or HLA- mismatched pair; obtaining hematopoietic cells from the donor comprising $CD34^+$ hematopoietic stem and progenitor cells, which may be referred to as HSPC; optionally isolating HSPC of the desired phenotype, e.g. $CD34^+$ cells, and formulating an effective dose of the HSPC; selecting a set of agents for non-genotoxic conditioning regimen on the recipient prior to infusion of the hematopoietic cells based on the number of donor cells administered to the recipient; the purity of the donor cells; the degree of major histocompatibility mismatch between donor and recipient; and the immune status of the recipient; administering the set of agents for non-genotoxic conditioning; infusing the hematopoietic cells; and monitoring the recipient for hematopoietic stem cell engraftment. The methods described herein apply to both HLA-matched and HLA-mismatched transplantation conditions, for example HLA-mismatched and not haploidentical transplantations, haploidentical transplantations; etc.

In some embodiments the HSPC are obtained from a donor hematopoietic cell sample. In some embodiments the hematopoietic cell sample is bone marrow. In some embodiments the HSPC are obtained from umbilical cord blood. In some embodiments, the hematopoietic cell sample is obtained by apheresis from donor mobilized peripheral blood. In some embodiments the HSPC are generated in vitro. The HSPC donor may be allogeneic or autologous, for example where the HSPC are genetically engineered by introduction or deletion of genetic material prior to re-infusion, for example during ex vivo culture. Allogeneic donors may be MHC matched to the recipient. The donor may be haploidentical or not haplo-identical to the recipient. The donor may be mismatched at one or more MHC loci, e.g. mismatched at 1, 2, 3, 4, 5 or 6 of the major loci for MHC matching.

The HSPC are optionally isolated from the hematopoietic cell sample for expression of CD34. The isolation may further comprise selection for expression of CD90. HSPC that are purified may be at least about 45% pure, as defined by the percentage of cells that are CD34+ in the population, may be at least about 50% pure, at least about 60% pure, at least about 70% pure, at least about 80% pure, at least about 90% pure. The effective dose of CD34+ cells may be from about $10^5$ to about $10^7$ CD34$^+$ cells/kg of recipient body weight, and may be at least about $5 \times 10^5$ CD34$^+$ cells/kg of recipient body weight, at least about $10^6$ CD34$^+$ cells/kg of recipient body weight, at least about $3 \times 10^6$ CD34$^+$ cells/kg of recipient body weight, at least about $5 \times 10^6$ CD34$^+$ cells/kg of recipient body weight, and may be $10^7$ CD34$^+$ cells/kg of recipient body weight or more. The dose of CD34+ cells; the purity of the cells, and the total number of cells delivered, i.e. the total dose of both CD34$^+$ and CD34$^-$ cells in the infusate, are important parameters for selection of the non-genotoxic conditioning agents.

The maximum number of CD3+ cells delivered with the HSPC composition may be not more than about $10^6$ CD3$^+$ cells/kg of recipient body weight, not more than about $5 \times 10^5$ CD3$^+$ cells/kg of recipient body weight, not more than about $3 \times 10^5$ CD3$^+$ cells/kg of recipient body weight, not more than about $10^4$ CD3$^+$ cells/kg of recipient body weight. The number of CD3$^+$ cells in the infusate may be a parameter for the selection of agents that inhibit cytotoxic lymphocytes, where increased numbers of CD3+ cells may require administration immediately prior to, or at the time of infusion, one or more agents that ablate T cells, including without limitation antibodies specific for CD3, for CD4, for CD8, etc.

In some embodiments, the transplantation is performed in the absence of myeloablative conditioning. In some embodiments the recipient is immunocompetent. The administration of the pre-transplantation conditioning regimen is repeated as necessary to achieve the desired level of ablation.

In some embodiments the CD47 blockade is accomplished by administering a soluble SIRPα polypeptide, which may be a high affinity SIRPα variant polypeptide. In other embodiments, antibodies specific for one or both of SIRPα and CD47 are administered.

Following transplantation with donor stem cells, the recipient may be a chimera or mixed chimera for the donor cells. The methods of the invention allow effective stem cell engraftment in the absence of non-selective ablation methods, e.g. radiation or chemotherapy, which have the undesirable effect of ablating differentiated cells involved in the function of the targeted tissue as well as undesirable side effects upon other tissues (e.g. on cells of the gastrointestinal system, hair growth), as well as increasing risk of secondary malignancies.

In one embodiment of the invention, the stem cells are one or more of autologous hematopoietic stem cells, genetically modified hematopoietic stem cells, and allogeneic hematopoietic stem cells, usually allogeneic stem cells. Such stem cells find use in the treatment of a variety of blood disorders, e.g. genetic disorders including aplastic anemia; sickle cell disease; thalassemias; severe immunodeficiency; bone marrow failure states, immune deficiencies, hemoglobinopathies, leukemias, lymphomas, immune-tolerance induction, genetic disorders treatable by bone marrow transplantation and other blood disorders, and the like.

The methods of the invention are also useful in the induction of tolerance in a patient, for example tolerance to donor tissue, e.g. in organ transplants; tolerance to autoantigens, e.g. in the context of treatment of autoimmune disease; and the like. In one embodiment of the invention, a method is provided for inducing tolerance in a patient, comprising administering to a patient administration of an agent that targets stem cells, including without limitation an antibody specific for c-kit and an agent that blockades CD47 activity; performed in combination with administration of an effective dose of one or a set of agents that reduce the number or activity of cytotoxic lymphocytes, which cytotoxic lymphocytes may include without limitation T cells, and natural killer (NK) cells. In some embodiments at least one agent is included that provides transient immune suppression of cytotoxic lymphocytes, including without limitation an agent that inhibits CD40/CD40L activity. In some embodiments the agent is an antibody specific to CD40L. In some embodiments the methods are performed in the absence of genotoxic conditioning. Following the conditioning regimen, the recipient is infused with an effective dose of hematopoietic stem and progenitor cells, thereby providing immune tolerance to the donor cells for future organ transplants.

BRIEF DESCRIPTION OF THE FIGURES

FIG. 1A 30e6 AKR×Hz F1 whole bone marrow was harvested and retro-orbitally transplanted into each Balb/c×C57BL/6 recipient. Chimerism was determined by CD45 allelic differences. FIG. 1B Each antibody was given on the marked day for conditioning. On day −8, 100ug of Clone 3 is given; on all subsequent days 500ug of Clone 3 is given. On day −6, 500ug of ACK2 is given. On day −1, 250ug of Tm-b1 is given. On day 0, 500ug of MR1 is given. FIG. 1C-1F. Mice were conditioned using different combinations of each antibody. Total donor chimerism was measured over 13 weeks FIG. 1C, in addition to T-cell FIG. 1D, B-cell FIG. 1E, and granulocytes FIG. 1F chimerism. Unchimeric mouse in ACK2+Clone 3+MR1 cohort is censored.

FIG. 2. 16 Week donor chimerism of antibody conditioned mice. Figure shows percentage of mice that are chimeric per cohort and the average levels of total donor, T-cell, B-cell, and granulocyte chimerism. Unchimeric mouse in ACK2+Clone 3+MR1 cohort is censored.

FIG. 3A Various amounts of AKRxHz F1 whole bone marrow was harvested and retroorbitally transplanted into each Balb/cxC57BL/6 recipient. Chimerism was determined by CD45 allelic differences. FIG. 3B Each antibody was given on the marked day for conditioning. On day −8, 100ug of Clone 3 is given; on all subsequent days 500ug of Clone 3 is given. On day −6, 500ug of ACK2 is given. On day −2, 250ug of Tm-b1 is given. On day 0, 500ug of MR1 is given. C-F. Each group was conditioned at the minimum with Clone 3, ACK2, and MR1. CD122 was also added to the two noted cohorts; thus receiving all four antibodies. Conditioned mice received either $30\times10^6$, $10^6$, $3\times10^6$ or $10^5$ whole bone marrow. Total donor chimerism was measured at 3 weeks FIG. 3C, in addition to T-cell FIG. 3D, B-cell FIG. 3E, and granulocytes FIG. 3F chimerism.

FIG. 4A-4I. A monoclonal antibody cocktail can induce long-term multi-lineage hematopoietic reconstitution. FIG. 4A Haploidentical transplantation schema using AKRB6F1 donors and CB6F1 recipients. FIG. 4B Flow cytometric analysis of MHC Class I on donor and recipient strains. FIG. 4C Dosing schedule for conditioning regimen. FIG. 4D Donor chimerism in the long-term HSC compartment (Lin− c-KIT+ Sca1+ CD150+ Flk2− CD34−) following Ab conditioning. FIG. 4E-4G Ab conditioning allows for long-term multi-lineage chimerism after WBM transplantation. FIG. 4H CBC following WBM Ab conditioning on Day 0. FIG. 4I Percentage of animals which are chimeric at various WBM doses, with or without NK cell depletion.

FIG. 5A-5F. A monoclonal antibody cocktail can induce long-term multi-lineage hematopoietic reconstitution of low dose purified HSCs. FIG. 5A Sorting scheme used to calculate and isolate LSK and c-KIT+ cells for transplantation. FIG. 5B Granulocyte chimerism following various hematopoietic cell grafts. FIG. 5C Dosing schedule for LSK Ab conditioning. FIG. 5D Mature immune cell population abundances in the bone marrow following LSK Ab conditioning. FIG. 5E Total peripheral blood donor chimerism following LSK transplantation. FIG. 5F Percentage of animals which are chimeric following exclusion of individual components of the LSK Ab cocktail.

FIG. 6A-6B Abundance of donor-reactive host T-cells in peripheral blood following WBM FIG. 6A and LSK FIG. 6B transplantation. FIG. 6C Ear-heart graft schematic. FIG. 6D Donor heart survival. FIG. 6E Gross examination, H&E, and IF of representative ear-heart grafts 34 days following tissue transplant.

FIG. 7A Transplantation schematic where DBA1/J are the donor and CB6F1 are the host. FIG. 7B Percent of donor engraftment following WBM and LSK transplantation after 8 weeks. FIG. 7C Overall survival of transplanted animals. FIG. 7D Overview describing an all-antibody conditioning regimen which can deplete endogenous HSCs, and provide transient immune suppression by targeting host T and NK cells.

FIG. 8A Sorting scheme to determine peripheral blood chimerism by CD45 allelic differences between the host and the donor. Multi-lineage peripheral blood chimerism 16 weeks following WBM transplant is shown for FIG. 8B T-cells, FIG. 8C B cells and FIG. 8D granulocytes.

FIG. 9. Peripheral blood donor chimerism following monotherapeutic conditioning using monoclonal antibodies.

FIG. 11. 16-week peripheral blood chimerism following variations of LSK Ab conditioning.

DETAILED DESCRIPTION OF THE EMBODIMENTS

Figures 1A, 1B:
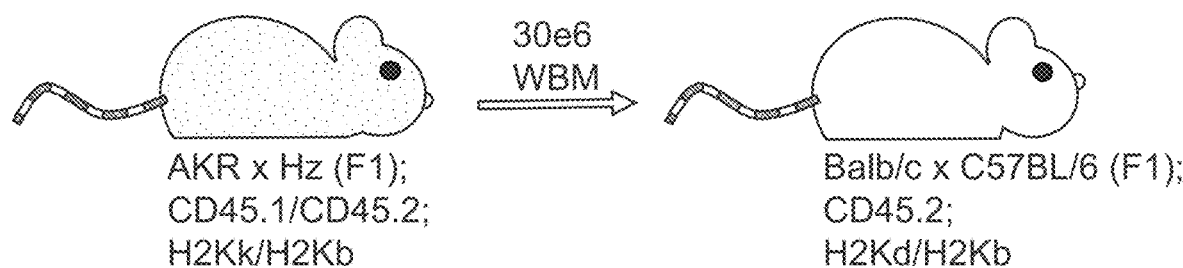
FIG. 1A-1F. ACK2, Clone 3, MR-1 and CD122 enable efficient engraftment of haploidentical whole bone marrow into immune competent animals.
Figure 1C:
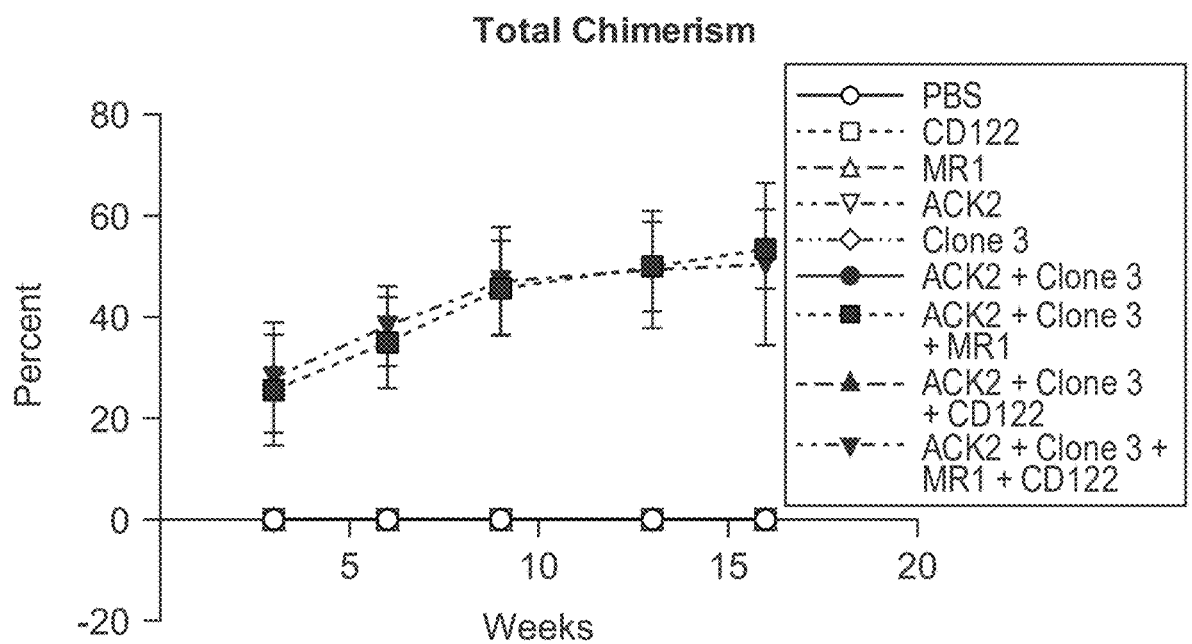
Figure 1D:
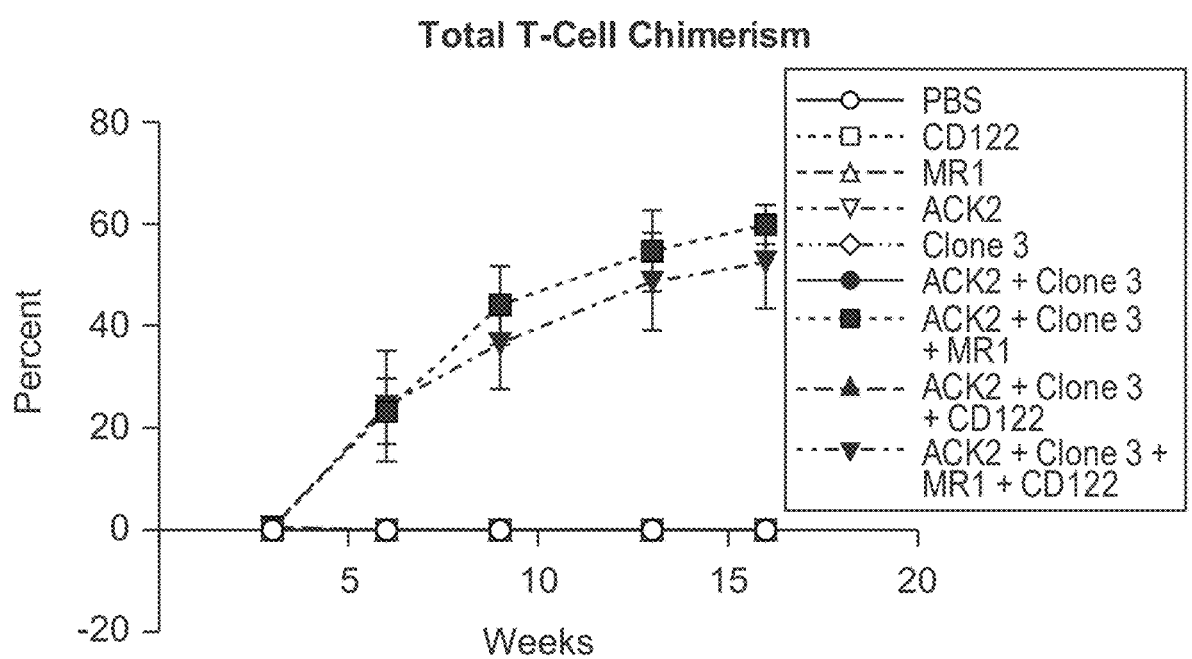
Figure 1E:
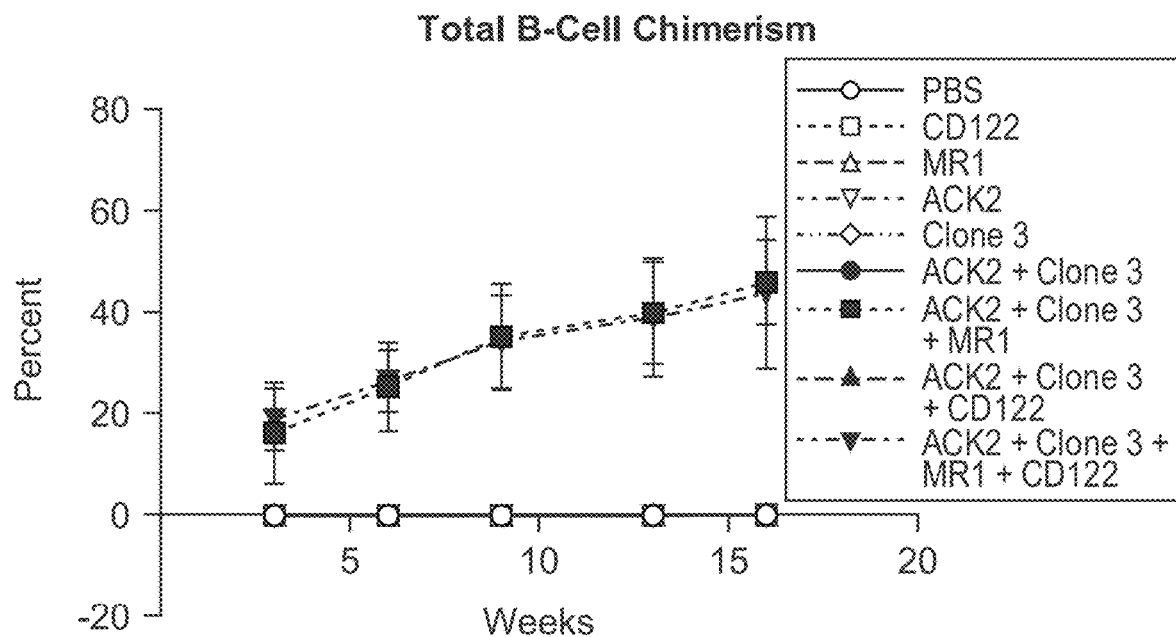
Figure 1F:
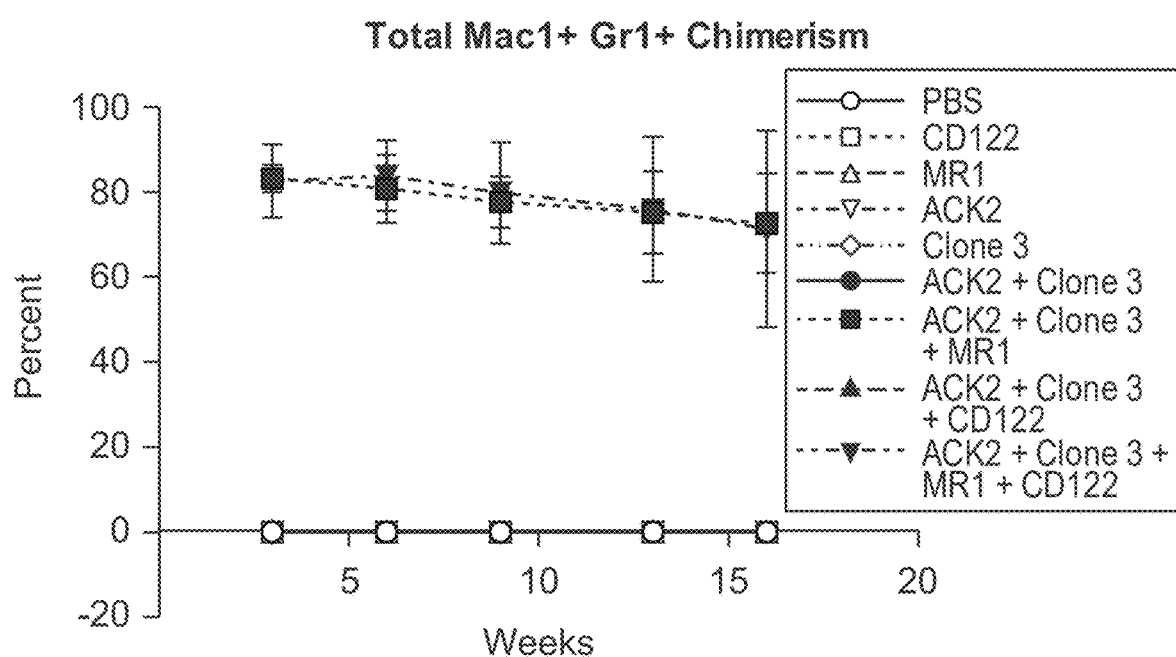
Figures 3A, 3B:
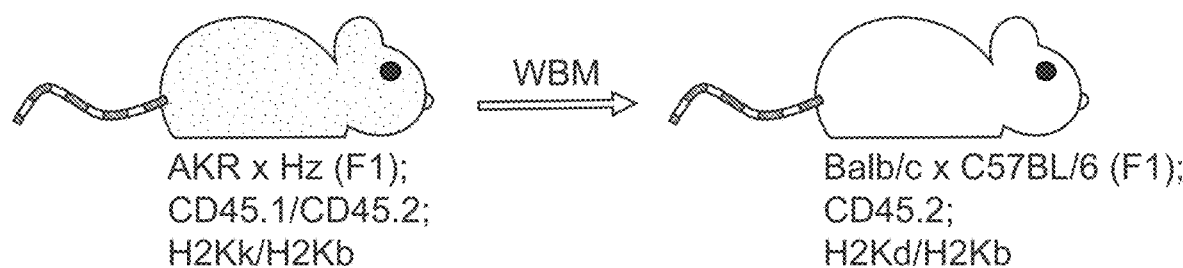
FIG. 3A-3F. NK-Cell depletion is required for engraftment of low cell dose bone marrow.
Figure 3C:
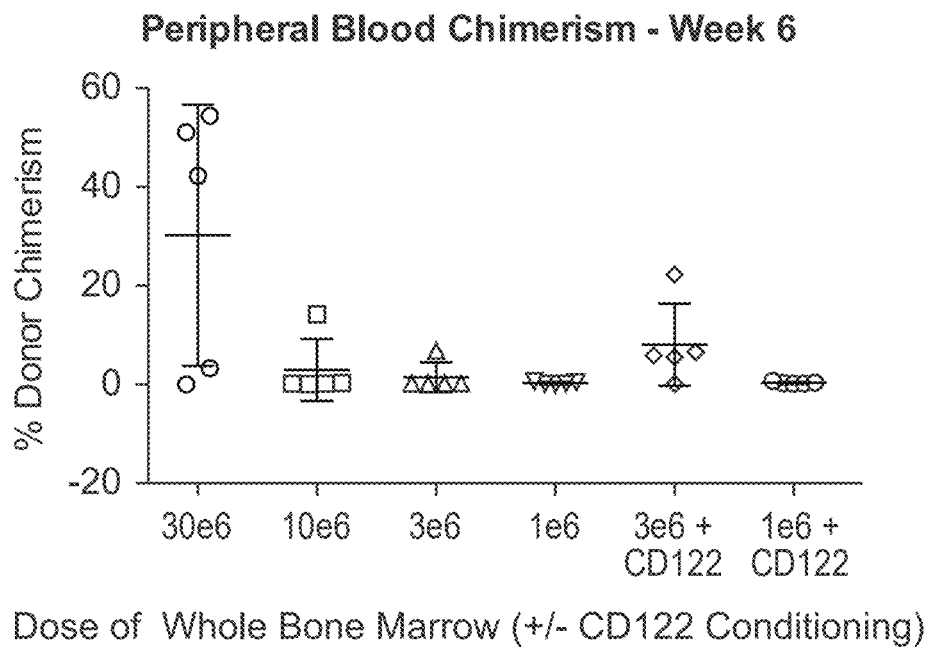
Figure 3D:
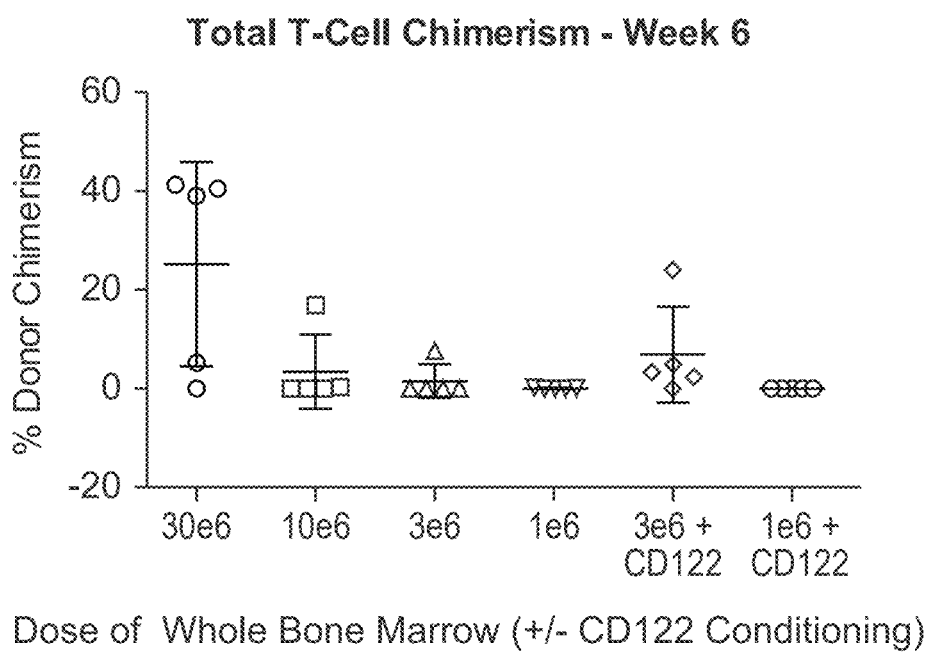
Figure 3E:
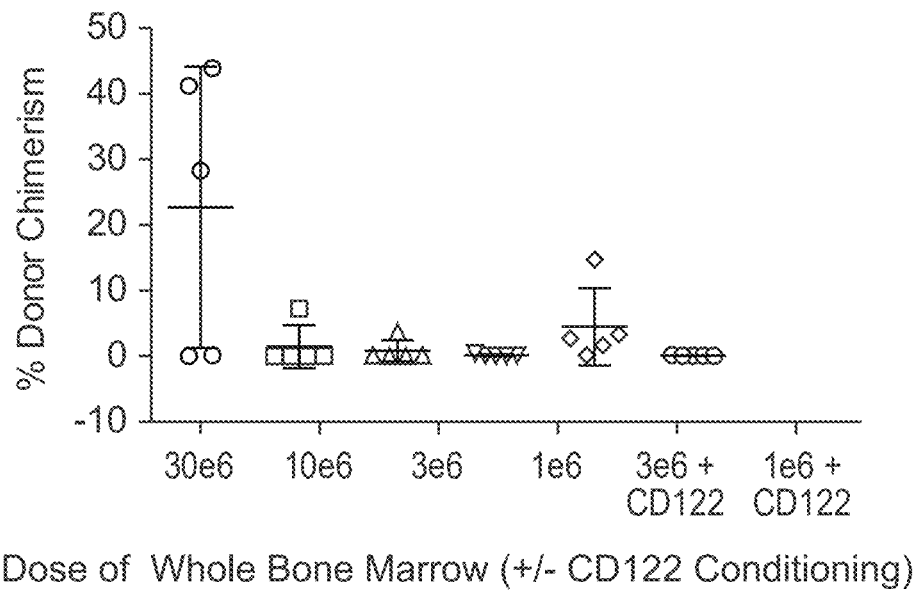
Figure 3F:
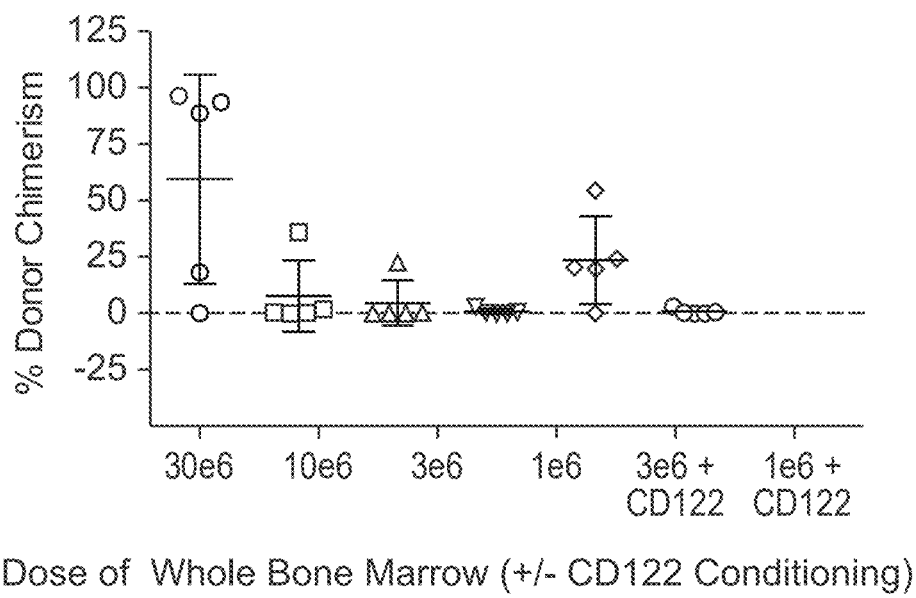

Methods are provided for the engraftment of stem cells in a subject by treatment with a non-genotoxic, non-myeloablative condition prior to infusion of a cellular composition comprising the stem and progenitor cells.

It is an objective of the present invention to provide a clinically applicable method of stem cell transplantation which facilitates engraftment and reconstitutes immunocompetence of the recipient without requiring radiotherapy or chemotherapy, or development of GVHD or graft rejection. Guidelines are also provided for selecting an appropriate conditioning regimen based on the nature and dose of the donor stem cell population, and the degree of HLA matching between the donor and recipient.

Aspects of the present invention are based on the discovery that a depletion of the endogenous stem cell niche that facilitates efficient engraftment of hematopoietic stem cells (HSCs) is accomplished by combining the use of an agent that targets the endogenous stem cells, e.g. anti-c-kit antibody, with an agent that enhances the killing of endogenous stem cells by blocking the interaction of CD47 and SIRPα, optionally combined with transient immunosuppression; and optionally combined with agents that deplete T and/or NK cells, allows safe engraftment of the donor cells. In particular, the present invention combines this improved selective ablation of endogenous stem cells, in combination with the administration to the recipient of exogenous stem cells, resulting in efficient, long-term engraftment and tolerance.

It is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

Conditioning regimen. Patients undergoing an allogeneic hemopoietic stem cell transplant (HSCT), are prepared with a so called conditioning regimen that may suppress the recipient's immune system and deplete endogenous stem cells, in order to allow engraftment of the donor stem cells.

The intensity of conventional conditioning regimens can vary significantly. Description of the regimens can refer to genotoxic or non-genotoxic regimens, which may overlap with reference to myeloablative or non-myeloablative regimens. See, for example, Bacigalupo et al. (2009) Biol Blood Marrow Transplant. 15(12):1628-1633, herein specifically incorporated by reference.

Genotoxic regimens comprise, at least in part, the administration of agents with direct or indirect effects on the DNA: the induction of mutations, mistimed event activation, and direct DNA damage leading to mutations. Examples of genotoxic agents include radiation and certain chemotherapeutic drugs, such as alkylating agents, intercalating agents and inhibitors of enzymes involved in DNA replication. The methods of the invention are non-genotoxic, and thus exclude the use of such agents.

Myeloablative conditioning regimens are combination of agents expected to produce profound pancytopenia and myeloablation within 1-3 weeks from administration; pancytopenia is long lasting, usually irreversible and in most instances fatal, unless hematopoiesis is restored by hemopoietic stem cell infusion. Examples include total body irradiation and/or administration of alkylating agents; fludarabine, dimethylbusulfan, etoposide (VP16); etc. There is significant overlap in genotoxic and myeloablative agents.

Non-myeloablative conditioning regiments typically cause minimal cytopenia, and little early toxicity, but are immunosuppressive to the extent that, when followed by administration of an effective dose of HSPC, will result in engraftment of donor lympho-hemopoietic stem cells.

The conditioning regimens provided herein are non-genotoxic and non-myeloablative, and primarily utilize targeted agents for depletion of endogenous cells that prevent engraftment, without causing log-lasting pancytopenia. The methods do not utilize genotoxic chemotherapeutic agents or radiation, although in some instances non-genotoxic, targeted immunosuppressive agents, such as cyclosporine A, corticosteroids, etc. can find use for transient immunosuppression.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

Stem cell markers. Exemplary markers for antibody mediated ablation of human hematopoietic stem cells include CD34; CD90 (thy-1); CD59; CD110 (c-mpl); c-kit (CD-117); etc. Markers useful for the ablation of mesodermal stem cells include FcγRll, FcγRlll, Thy-1, CD44, VLA-4α, LFA-1β, HSA, ICAM-1, CD45, Aa4.1, Sca-1, etc. Neural crest stem cells may be positively selected with antibodies specific for low-affinity nerve growth factor receptor (LNGFR). Neural stem/progenitor cells have been described in the art, and their use in a variety of therapeutic protocols has been widely discussed. For example, inter alia, Uchida et al. (2000) Proc Natl Acad Sci USA. 97(26):14720-5. U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80; each herein specifically incorporated by reference. Human mesenchymal stem cells may be ablated using the markers such as SH2 (CD105), SH3 and SH4 and Stro-1.

In one embodiment of the invention, the marker for depletion is c-kit (CD117). CD117 is a receptor tyrosine kinase type Ill, which binds to stem cell factor (a substance that causes certain types of cells to grow), also known as "steel factor" or "c-kit ligand". When this receptor binds to stem cell factor (SCF) it forms a dimer that activates its intrinsic tyrosine kinase activity, that in turn phosphorylates and activates signal transduction molecules that propagate the signal in the cell. See, for example, the human refseq entries Genbank NM_000222; NP_000213. CD117 is an important cell surface marker used to identify certain types of hematopoietic (blood) progenitors in the bone marrow. Hematopoietic stem cells (HSC), multipotent progenitors (MPP), and common myeloid progenitors (CMP) express high levels of CD117. A number of antibodies that specifically bind human CD117 are known in the art and commercially available, including without limitation SR1, 2B8, ACK2, YB5-B8, 57A5, 104D2, etc. Of interest is the humanized form of SR1, AMG 191, described in U.S. Pat. Nos. 8,436,150, and 7,915,391 which is an aglycosylated IgG1 humanized antibody.

An effective dose of an anti-CD117 antibody may be administered in one or more doses, including a single dose, which may be at least about one week prior to transplantation, at least about 5 days prior to transplantation, at least about 3 days prior to transplantation. The period of time between dosing and transplantation is sufficient to substantially eliminate the anti-CD117 antibody from the circulation of the recipient. For example the decrease in peak serum levels following administration is usually the time sufficient for the level to decrease as least about 10-fold from peak levels, usually at least about 100-fold, 1000-fold, 10,000-fold, or more. It is preferable to introduce the donor stem cells within the empty niche "window" following the washout period, usually within about 3 days, about 2 days, about 1 day, or at the time of clearance.

In some embodiments, an effective dose of an anti-CD117 antibody is up to about 10 mg/kg, up to about 5 mg/kg; up to about 1 mg/kg, up to about 0.5 mg/kg; up to about 0.1 mg/kg; up to about 0.05 mg/kg; where the dose may vary with the specific antibody and recipient.

Anti-CD47 agent. As used herein, the term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

The effective dose of an anti-CD47 agent can vary with the agent, but will generally range from up to about 50 mg/kg, up to about 40 mg/kg, up to about 30 mg/kg, up to about 20 mg/kg, up to about 10 mg/kg, up to about 5 mg/kg; up to about 1 mg/kg, up to about 0.5 mg/kg; up to about 0.1 mg/kg; up to about 0.05 mg/kg; where the dose may vary with the specific antibody and recipient. Agents that bind to CD47, e.g. soluble SIRPα polypeptides and anti-CD47 antibodies, may be administered at higher doses due to the larger number of CD47 expressing cells in the body.

The anti-CD47 agent may be administered one or a plurality of days prior to transplantation, and in some embodiments is administered daily for a period of from about 1, about 2, about 3, about 4, about 5, about 6, about 7 or more days, i.e. from about 1 to 7 days, from about 1 to 5 days, from about 1 to 3 days, etc. As with the anti-c-kit agent, targeting CD47 can affect the donor stem cells after infusion, and therefore a wash-out period is required before infusion of hematopoietic cells. The washout period may be shorter than with the c-kit antibody, but is typically at least about 24 hours, at least 36 hours, at least 48 hours, and may be up to about one week, up to about 5 days, up to about 3 days, etc.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent. In an exemplary assay, target cells are incubated in the presence or absence of the candidate agent. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1 2004). Thus, in some embodiments, the anti-CD47 agent does not directly induce cell death of a CD47-expressing cell.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα.

In some embodiments, a subject anti-CD47 agent is a "high affinity SIRPα reagent", which includes SIRPα -derived polypeptides and analogs thereof (e.g., CV1-hIgG4, and CV1 monomer). High affinity SIRPα reagents are described in international application PCT/US13/21937, which is hereby specifically incorporated by reference. High affinity SIRPα reagents are variants of the native SIRPα protein. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

Optionally the SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

Anti-CD47 antibodies. In some embodiments, a subject anti-CD47 agent is an antibody that specifically binds CD47

(i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to the native CD47 sequence.

Transient immunosuppressive agent. A transient immunosuppressive agent blocks the activity of immune cells, particularly T lymphocytes, for a short period of time, usually the period of time at or shortly before the administration of the donor cells. Transient immunosuppression, i.e. an effective serum level of the immunosuppressive agent(s) may be maintained for at least about 3 days, at least about 1 week, at least about 2 weeks, at least about 3 weeks, at least about 4 weeks, at least about 5 weeks, at least about 6 weeks, and may be maintained for up to 1 month, up to 2 months, up to 3 months, up to 4 months, up to 5 months, up to 6 months, or more. In some embodiments a single dose of the agent is administered immediately prior to, or concomitantly, with the donor cells. Such agents are usually suppressive, without ablation of the immune cell population. The initial dose of the agent may be made within about 3 days, within about 2 days, within about 1 day, or at the time of administration of the donor cells.

Transient immunosuppression can be achieved by administration of a pharmacologic immunosuppressive agent, including without limitation calcineurin inhibitors, which combine with binding proteins to inhibit calcineurin activity, and which include, for example, tacrolimus, cyclosporine A, etc. Levels of both cyclosporine and tacrolimus must be carefully monitored. Initially, levels can be kept in the range of 10-20 ng/mL, but, after 3 months, levels may be kept lower (5-10 ng/mL) to reduce the risk of nephrotoxicity. Other pharmacologic agents for this purpose include steroids, azathioprine, mycophenolate mofetil, and sirolimus, etc.

In some embodiments a transient immunosuppressive agent blocks the interaction of CD40 and CD40 ligand. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L).

"CD40 ligand" ("CD40L", also called "CD154") is a type II transmembrane protein. CD40L was originally considered restricted to activated T lymphocytes, functioning as a mediator of T cell-dependent B cell activation, proliferation, and differentiation. Expression of CD40L plays a functional role as a central mediator of immunity and inflammation of the tumor necrosis factor (TNF) gene superfamily. CD40/CD40L interaction is essential for the development of thymus-dependent humoral immune responses. CD40L modulates physiologic processes, such as T cell-mediated effector functions and general immune responses required for appropriate host defense, but also triggers the expression of pro-inflammatory mediators, such as cytokines, adhesion molecules, and matrix degrading activities, all of which are associated with the pathogenesis of chronic inflammatory diseases, e.g., autoimmune disorders, arthritis, atherosclerosis, and cancer.

Given its critical role in mediating many aspects of immune responses, the CD40/CD40L pathway provides a therapeutic target for the prevention of transplantation rejection. Interrupting the CD40/CD40L signal pathway with anti-CD40L antibody can be effective in preventing acute allograft rejection and alloantibody responses in animal models and in clinical use. Subsequent studies have demonstrated the beneficial effect of anti-CD40L on the prolongation of graft survival in a number of rodent models (islet, limb, corneal and marrow).

As used herein, the term "anti-CD40L agent" or "agent that provides for CD40L blockade" refers to any agent that reduces the binding of CD40L (e.g., on a target cell) to CD40. Non-limiting examples of suitable anti-CD40L reagents include anti-CD40 antibodies, and anti-CD40L antibodies or antibody fragments. Agents of interest also include, without limitation, fragments of antibodies and small molecules. For example, CDP7657 is a high affinity PEGylated monovalent Fab' anti-CD40L antibody fragment. An effective dose of an antibody may be up to about 50 mg/kg, up to about 25 mg/kg; up to about 10 mg/kg, up to about 5 mg/kg; up to about 1 mg/kg; up to about 0.5 mg/kg; or less, where the dose may vary with the specific antibody and recipient. As an alternative to antibodies, small molecule inhibitors are described, for example in Chen et al. (2017) J. Med. Chem. 60, 8906-8922, herein specifically incorporated by reference.

T cell ablation. For some transplant situations, as outlined in Table 1, it is desirable to delete endogenous T cells. In some embodiments the ablative agent is specific for T cells, in others it also acts on NK cells. Antibodies that target T cells include, for example, antibodies specific for CD2, CD3, CD4, CD8, CD52 (campath), CD45, and ATG.

With respect to timing, a T cell depleting agent is desirably active in the period of time at or shortly before the administration of the donor cells. Therapeutic levels of the depletion agent may be maintained for at least about 3 days, at least about 1 week, at least about 2 weeks, at least about 3 weeks, at least about 4 weeks, at least about 5 weeks, at least about 6 weeks, and may be maintained for up to 1 month, up to 2 months, up to 3 months, up to 4 months, up to 5 months, up to 6 months, or more following administration of the donor cells. In some embodiments a dose of the agent is administered within about 3 days, within about 2 days, within about 1 day, or at the time of administration of the donor cells, and depending on the antibody, may be administered daily for several days, e.g. 2, 3 4 etc., prior to infusion. An effective dose of an antibody may be up to about 50 mg/kg, up to about 25 mg/kg; up to about 10 mg/kg, up to about 5 mg/kg; up to about 1 mg/kg; up to about 0.5 mg/kg; or less, for example up to about 100 g/kg, up to about 50 µg/kg, up to about 10 µg/kg, up to about 1 µg/kg, where the dose may vary with the specific antibody and recipient. Antibody-based therapy may use monoclonal (e.g., muromonab-CD3) or polyclonal antibodies; anti-CD25 antibodies (e.g., basiliximab, daclizumab), etc. Antibodies include, for example, an ATG preparation, a-KT3, BTI-322® (U.S. Pat. No. 5,730,979 the disclosure of which is hereby incorporated by reference).

Multiple anti-human CD3 mAb are in clinical development, including Teplizumab, and MGA031, is a humanized IgG1 antibody that was developed by grafting the complementarity determining region of OKT3 into a human IgG1 backbone. Otelixizumab (ChAglyCD3, TRX4, GSK2136525) is derived from the rat antibody YTH12.5, and is a humanized IgG1 with a single mutation in the γ1 Fc portion to avoid glycosylation and thus inhibit FcR binding. Visilizumab (Nuvion, HuM291) is a humanized IgG2 antibody rendered non mitogenic by two point mutations in its Fc region. Foralumab (28F11-AE; NI-0401) is an entirely human anti-CD3 mAb.

A useful agent for depletion of T cells and NK cells is an anti-CD52 antibody, exemplified by the clinically approved antibody Campath (alemtuzumab), which is a recombinant DNA-derived humanized monoclonal antibody directed against the 21-28 kD cell surface glycoprotein, CD52. Campath-1H is an IgG1 kappa antibody with human variable framework and constant regions, and complementarity-determining regions from a murine (rat) monoclonal antibody (Campath-1G). Campath may be administered, for example, at the currently accepted clinical dose, e.g. escalating to the maximum single dose of 30 mg over a period of from about 3 to about 7 days.

NK cell ablation. For some transplant situations, as outlined in Table 1, it is desirable to also delete endogenous NK cells. As indicated above, some agents act on both T cells and NK cells, e.g. antibodies to CD2, CD52, etc. Other agents are specific for NK cells and may be administered in combination with T cell targeted agents. Antibodies that selectively target NK cells include, for example, antibodies specific for CD122 and CD56.

With respect to timing, an NK cell depleting agent is desirably active in the period of time at or shortly before the administration of the donor cells. Therapeutic levels of the depletion agent may be maintained for at least about 3 days, at least about 1 week, at least about 2 weeks, at least about 3 weeks, at least about 4 weeks, at least about 5 weeks, at least about 6 weeks, and may be maintained for up to 1 month, up to 2 months, up to 3 months, up to 4 months, up to 5 months, up to 6 months, or more following administration of the donor cells. In some embodiments a dose of the agent is administered within about 3 days, within about 2 days, within about 1 day, or at the time of administration of the donor cells, and depending on the antibody, may be administered daily for several days, e.g. 2, 3, 4 etc., prior to infusion. An effective dose of an antibody may be up to about 50 mg/kg, up to about 25 mg/kg; up to about 10 mg/kg, up to about 5 mg/kg; up to about 1 mg/kg; up to about 0.5 mg/kg; or less, for example up to about 100 µg/kg, up to about 50 µg/kg, up to about 10 µg/kg, up to about 1 µg/kg, where the dose may vary with the specific antibody and recipient.

"CD122" (also called "interleukin-2 receptor subunit beta", IL2RB) is a type I membrane protein. CD122 is a subunit of the interleukin 2 receptor (IL2R), which is involved in T cell-mediated immune responses, and is present in 3 forms with respect to ability to bind interleukin 2. The low affinity form of IL2R is a monomer of the alpha subunit and is not involved in signal transduction. The intermediate affinity form consists of an alpha/beta subunit heterodimer, while the high affinity form consists of an alpha/beta/gamma subunit heterotrimer. Both the intermediate and high affinity forms of the receptor are involved in receptor-mediated endocytosis and transduction of mitogenic signals from interleukin 2. The use of alternative promoters results in multiple transcript variants encoding the same protein.

As used herein, the term "anti-CD122 agent" or "agent that provides for CD122 blockade" refers to any agent that depletes CD122 positive cells, including natural killer (NK) cells. Non-limiting examples of suitable anti-CD122 reagents include anti-IL-2 antibodies, and anti-CD122 antibodies or antibody fragments.

Antibodies that target CD56 are in clinical development and find use in NK cell depletion. For example, IMGN901 is a CD56-targeting antibody-drug conjugate designed for selective delivery of the cytotoxic maytansinoid DM1 with a maximum tolerated dose (MTD) of about 75 mg/m$^2$, and which may be administered at doses of, for example, from about 1 to about 60 mg/m$^2$.

"Major histocompatibility complex antigens" ("MHC", also called "human leukocyte antigens", HLA) are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells. Both have been implicated in the rejection of transplanted organs.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules. The genes most important for HLA typing are the six MHC Class I and Class II proteins, two alleles for each of HLA-A; HLA-B and HLA-DR.

The HLA genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA matched" refers to a donor recipient pair in which none of the HLA antigens are mismatched between the donor and recipient. HLA matched (i.e., where all of the 6 alleles are matched) donor/recipient pairs have a decreased risk of graft v. host disease (GVHD) relative to mismatched pairs (i.e. where at least one of the 6 alleles is mismatched). HLA haploidentical refers to a match where one chromosome is matched at least at HLA-A; HLA-B and HLA-DR, and may be matched at minor histocompatibility loci on the chromosome; but is not necessarily matched on the second chromosome. Such donors frequently occur in families, e.g. a parent is haploidentical to a child; and siblings may be haploidentical.

As used herein, the term "HLA mismatched" refers to a donor recipient pair in which at least one HLA antigen, in particular with respect to HLA-A, HLA-B and HLA-DR, is mismatched between the donor and recipient. In some cases, one haplotype is matched and the other is mismatched. This situation is frequently found with organs from living or deceased donors. HLA mismatched donor/recipient pairs have an increased risk of GVHD relative to perfectly matched pairs (i.e. where all 6 alleles are matched).

HLA alleles are typically noted with a variety of levels of detail. Most designations begin with HLA- and the locus name, then * and some (even) number of digits specifying the allele. The first two digits specify a group of alleles. Older typing methodologies often could not completely distinguish alleles and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S may follow an allele's designation to specify an expression level or other non-genomic data known about it. Thus, a completely described allele may be up to 9 digits long, not including the HLA-prefix and locus notation.

As used herein, a "recipient" is an individual to whom an organ, tissue or cells from another individual (donor), commonly of the same species, has been transferred. For the purposes of the present disclosure, a recipient and a donor are either HLA-matched or HLA-mismatched.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies for endogenous stem cell ablation and transient immunosuppression may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies. The cross-linking of Fc receptors signals the effector cells to kill the target cells by cytolysis or apoptosis. In one embodiment, the induction is achieved via antibody-dependent cellular cytotoxicity (ADCC). In alternative embodiments, the antibodies are active in growth inhibition of the targeted cells, an ablation is achieved by interfering with growth factor signaling, e.g. antibodies specific for growth factor receptors such as c-kit.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$—$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest for ablation may be tested for their ability to induce ADCC (antibody-dependent cellular cytotoxicity). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.). Preferably, the antibodies of the present invention induce at least 10%, 20%, 30%, 40%, 50%, 60%, or 80% cytotoxicity of the target cells.

In some embodiments, the antibody is conjugated to an effector moiety. The effector moiety can be any number of molecules, including labeling moieties such as radioactive labels or fluorescent labels, or can be a cytotoxic moiety. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, saporin, auristatin-E and the like. Cytotoxic agents also include radiochemicals made by conjugating radioisotopes to antibodies. Targeting the cytotoxic moiety to transmembrane proteins serves to increase the local concentration of the cytotoxic moiety in the targeted area.

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages.

For engraftment purposes, a composition comprising hematopoietic stem cells, is administered to a patient. Such methods are well known in the art. The stem cells are optionally, although not necessarily, purified. Abundant reports explore various methods for purification of stem cells and subsequent engraftment, including flow cytometry; an isolex system (Klein et al. (2001) Bone Marrow Transplant. 28(11):1023-9; Prince et al. (2002) Cytotherapy 4(2): 137-45); immunomagnetic separation (Prince et al. (2002) Cytotherapy 4(2):147-55; Handgretinger et al. (2002) Bone Marrow Transplant. 29(9):731-6; Chou et al. (2005) Breast Cancer. 12(3):178-88); and the like. Each of these references is herein specifically incorporated by reference, particularly with respect to procedures, cell compositions and doses for hematopoietic stem cell transplantation.

Hematopoietic stem cells can be obtained by harvesting from bone marrow or from peripheral blood. Bone marrow is generally aspirated from the posterior iliac crests while the donor is under either regional or general anesthesia. Additional bone marrow can be obtained from the anterior iliac crest. A dose of $1\times10^8$ and $2\times10^8$ marrow mononuclear cells per kilogram is generally considered desirable to establish engraftment in autologous and allogeneic marrow transplants, respectively. Bone marrow can be primed with granulocyte colony-stimulating factor (G-CSF; filgrastim [Neupogen]) to increase the stem cell count. Reference to "whole bone marrow" for the purposes described herein generally refers to a composition of mononuclear cells derived from bone marrow that have not been selected for specific immune cell subsets. "Fractionated bone marrow" may be, for example, depleted of T cells, e.g. $CD8^+$ cells, $CD52^+$ cells, $CD3^+$ cells, etc.; enriched for CD34+ cells, etc.

Hematopoietic stem cells are also obtained from cord blood. Cord blood is an almost unlimited source of hematopoietic stem cells for allogeneic hematopoietic stem cell transplant. Cord blood banks (CBB) have been established for related or unrelated UCBT with more than 400,000 units available and more than 20,000 umbilical cord blood transplants performed in children and in adults. UCB hematopoietic progenitors are enriched in primitive stem/progenitor cells able to produce in vivo long-term repopulating stem cells. However, the number of cells available from any single donor can be relatively low in comparison with other sources.

Mobilization of stem cells from the bone marrow into peripheral blood by cytokines such as G-CSF or GM-CSF has led to the widespread adoption of peripheral blood progenitor cell collection by apheresis for hematopoietic stem cell transplantation. The dose of G-CSF used for mobilization is 10 µg/kg/day. In autologous donors who are heavily pretreated, however, doses of up to 40 µg/kg/day can be given. Mozobil may be used In conjunction with G-CSF to mobilize hematopoietic stem cells to peripheral blood for collection.

The dose of stem cells administered may depend on the desired purity of the infused cell composition, and the source of the cells. Current guidelines indicate that the minimum dose required for engraftment is $1-2\times10^6$ $CD34^+$ cells/kg body weight for autologous and allogeneic transplants. Higher doses can include, for example, $3\times10^6$, $4\times10^6$, $5\times10^6$, $6\times10^6$, $7\times10^6$, $8\times10^6$, $9\times10^6$, $10^7$ or more. Frequently the dose is limited by the number of available cells. Typically, regardless of the source, the dose is calculated by the number of CD34+ cells present. The percent number of $CD34^+$ cells can be low for unfractionated bone marrow or mobilized peripheral blood; in which case the total number of cells administered is much higher.

The CD34+ cells may be selected by affinity methods, including without limitation magnetic bead selection, flow cytometry, and the like from the donor hematopoietic cell sample. The HSPC composition may be at least about 50% pure, as defined by the percentage of cells that are CD34+ in the population, may be at least about 75% pure, at least about 85% pure, at least about 95% pure, or more. Preferable a maximum number of CD3+ cells delivered with the HSPC composition is not more than about $10^6$ CD3+ cells/kg of recipient body weight, not more than about $10^5$ $CD3^+$ cells/kg of recipient body weight, not more than about 104 $CD3^+$ cells/kg of recipient body weight. Alternatively cell populations may be tandemly selected for expression of CD34 and CD90, which cell populations may be highly purified, e.g. at least about 85% $CD34+CD90^+$ cells, at least about 90% $CD34+CD90^+$ cells, at least about 95% CD34+ $CD90^+$ cells and may be up to about 99% $CD34+CD90^+$ cells or more. Alternatively unmanipulated bone marrow or mobilized peripheral blood populations are used.

Hematopoietic stem cells can also be generated in vitro, for example from pluripotent embryonic stem cells, induced pluripotent cells, and the like. For example, see Sugimura et al. (2017) Nature 545:432-438, herein specifically incorporated by reference, which details a protocol for generation of hematopoietic progenitors.

The cells which are employed may be fresh, frozen, or have been subject to prior culture. They may be fetal, neonate, adult, etc. Hematopoietic stem cells may be obtained from fetal liver, bone marrow, blood, particularly G-CSF or GM-CSF mobilized peripheral blood, or any other conventional source. Cells for engraftment are optionally isolated from other cells, where the manner in which the stem cells are separated from other cells of the hematopoietic or other lineage is not critical to this invention. If desired, a substantially homogeneous population of stem or progenitor cells may be obtained by selective isolation of cells free of markers associated with differentiated cells, while displaying epitopic characteristics associated with the stem cells.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is constitutive, pan-specific, specifically active in a differentiated cell type, etc. Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells. Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line. The vectors may include genes that must later be removed, e.g. using a recombinase system such as Cre/Lox, or the cells that express them destroyed, e.g. by including genes that allow selective toxicity such as herpesvirus TK, bcl-xs, etc.

Chimerism, as used herein, generally refers to chimerism of the hematopoietic system, unless otherwise noted. A determination of whether an individual is a full chimera, mixed chimera, or non-chimeric made be made by an analysis of a hematopoietic cell sample from the graft recipient, e.g. peripheral blood, bone marrow, etc. as known in the art. Analysis may be done by any convenient method of typing. In some embodiments the degree of chimerism amongst all mononuclear cells, T cells, B cells, CD56+NK cells, and CD15+ neutrophils is regularly monitored, using PCR with probes for microsatellite analysis. For example, commercial kits that distinguish polymorphisms in short terminal repeat lengths of donor and host origin are available. Automated readers provide the percentage of donor type cells based on standard curves from artificial donor and host cell mixtures.

Individuals who exhibited more than a 95% donor cells in a given blood cell lineage by such analysis at any time post-transplantation are referred to as having full donor chimerism in this transplant patient group. Mixed chimerism is defined as greater than 1% donor but less than 95% donor DNA in such analysis. Individuals who exhibit mixed chimerism may be further classified according to the evolution of chimerism, where improving mixed chimerism is defined as a continuous increase in the proportion of donor cells over at least a 6-month period. Stable mixed chimerism is defined as fluctuations in the percentage of recipient cells over time, without complete loss of donor cells.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

Additional terms. The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

Methods for Engraftment

The methods of the invention provide for improved engraftment of stem cells after transplantation into a recipient. The recipient may be immunocompetent, and the transplantation may be performed in the absence of myeloablative conditioning, i.e. in the absence of radiation and/or chemotherapeutic drugs. The recipient is conditioned with the combined administration a set of agents selected according to the cells and HLA match. The selection of agents is indicated in Table 1, which provides guidelines for optimized conditioning protocols. A "+" indicates that for the indicated agent, HLA match and cell source, the agent should be included; and a "−" indicates it is not required, although optionally can be included. As disclosed above, certain agents can deplete both T cells and NK cells, and therefore only the single agent is required for both. The timing and dose for the different agents is as indicated above. The conditioning regimens of the invention selectively ablate endogenous stem cells and provide for suitable, selected suppression of endogenous immune responses, which allow for engraftment even in non-matched recipients.

TABLE 1

| | Autologous | | | | Haploindentical | | | | Unmatched/Xeno | | | |
|---|---|---|---|---|---|---|---|---|---|---|---|---|
| | SC@ | TI# | NK* | T& | SC@ | TI# | NK* | T& | SC@ | TI# | NK* | T& |
| Bone Marrow high dose | + | − | − | − | + | + | − | − | + | + | + | + |

TABLE 1-continued

|  | Autologous | | | | Haploindentical | | | | Unmatched/Xeno | | | |
| --- | --- | --- | --- | --- | --- | --- | --- | --- | --- | --- | --- | --- |
|  | SC@ | TI# | NK* | T& | SC@ | TI# | NK* | T& | SC@ | TI# | NK* | T& |
| Bone marrow low dose | + | − | − | − | + | + | − | − | + | + | + | + |
| Cord Blood | + | − | − | − | + | + | + | + | + | + | + | + |
| Unfractionated PBMC | + | − | − | − | + | + | + | + | + | + | + | + |
| PBMC enriched HSPC | + | − | − | − | + | + | + | + | + | + | + | + |
| engineered cell populations | + | + | − | − | + | + | + | + | + | + | + | + |

SC@ administer a combination of agents to deplete endogenous stem cells, and allow a washout period prior to infusion of the indicated exogenous cell population.
TI# administer an agent active at the time of infusion to provide for transient immunosuppression
NK* administer an agent prior to and optionally at the time of infusion to deplete NK cells
T& administer an agent prior to and optionally at the time of infusion to deplete T cells
Bone marrow high dose is equivalent to ≥ 150 × 10$^7$ CD34$^+$ cells/kg
Bone marrow low dose is equivalent to > 150 × 10$^6$ CD34$^+$ cells/kg
PBMC enriched HSPC have a purity of greater than 50% CD34$^+$ cells
Engineered cell populations are genetically altered ex vivo, or derived from pluripotent progenitors in vitro Following the conditioning regimen, an effective dose of a cellular composition comprising exogenous stem cells is administered to the recipient during a period of transient immunosuppression. The stem cells may be autologous, allogeneic or xenogeneic, including without limitation allogeneic haploidentical stem cells, mismatched allogeneic stem cells, genetically engineered autologous cells, etc.

The infusion of HSPC is a relatively simple process that is performed at the bedside. A bone marrow product is generally used fresh and is infused through a central vein over a period of several hours. Autologous products are frequently cryopreserved; if so they are thawed at the bedside and infused rapidly over a period of several minutes. PBMC may be stored briefly overnight or frozen.

Where the donor is allogeneic to the recipient, the HLA type of the donor and recipient may be tested for a match, or haploidentical cells are used. HLA-haploidentical donors can be manipulated by CD34 or CD34CD90 selection. Moreover, HLA-haplo-identical donors are now widely used (and may surpass HLA-identical) for other indications. For HLA matching, traditionally, the loci critical for matching are HLA-A, HLA-B, and HLA-DR. HLA-C and HLA-DQ are also now considered when determining the appropriateness of a donor. A completely matched sibling donor is generally considered the ideal donor. For unrelated donors, a complete match or a single mismatch is considered acceptable for most transplantation, although in certain circumstances, a greater mismatch is tolerated. Preferably matching is both serologic and molecular. Where the donor is umbilical cord blood the degree of tolerable HLA disparity is much greater, and a match of 3-4 out of the 6 HLA-A, HLA-B and HLA-DRB1 antigens is sufficient for transplantation. Immunocompetent donor T cells may be removed using a variety of methods to reduce or eliminate the possibility that graft versus host disease (GVHD) will develop.

In some embodiments, success of the procedure is monitored by determining the presence of host-derived myeloid cells, e.g. CD15$^+$ cells, in circulation of the recipient. Blood myeloid chimerism is indicator of true HSC engraftment due to the short-lived nature of myeloid cells. After about 8 weeks post-HCT, methods described herein have provided for measurable and sustained levels of blood myeloid chimerism, e.g. of at least about 1% donor type CD15$^+$ cells, at least about 2% donor type CD15$^+$ cells, at least about 4% donor type CD15$^+$ cells, at least about 8% donor type CD15$^+$ cells, or more.

The conditioning agents, which may be provided in the absence of myeloablative radiation or chemotherapy, are administered according to the specific requirements discussed above. Some agents are administered to be active following administration of the HSPC, while other agents require a washout period.

The transient immunosuppressive agent is provided in a dose that decreases activated T cell activity by at least 10-fold, at least 100-fold, at least 1000-fold, at least 100,000-fold or more. The effective dose will depend on the individual and the specific agent, but will where the agent is an antibody, the dose may be at least about 50 µg/kg body weight, at least about 250 µg/kg, at least about 500 µg/kg, at least about 750 µg/kg, at least about 1 mg/kg, and up to about 2.5 mg/kg, up to about 5 mg/kg, up to about 7.5 mg/kg, up to about 10 mg/kg, up to about 15 mg/kg, up to about 25 mg/kg, up to about 50 mg/kg, up to about 100 mg/kg.

The conditioning agents are formulated in pharmaceutical compositions. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). As is known in the art, adjustments for patient condition, systemic versus localized delivery, as well as the age, body weight, general health, sex, diet, time of administration, drug interaction and the severity of the condition may be necessary, and will be ascertainable with routine experimentation by those skilled in the art.

The administration of the agents can be done in a variety of ways as discussed above, including, but not limited to, orally, subcutaneously, intravenously, intranasally, transdermally, intraperitoneally, intramuscularly, or intraocularly. Antibodies may be delivered by intravenous injection.

In one embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

The compositions containing ablative agents, e.g. antibodies, soluble SIRPα, etc. can be administered for therapeutic treatment. Compositions are administered to a patient in an amount sufficient to substantially ablate targeted endogenous stem cells, as described above. An amount adequate to accomplish this is defined as a "therapeutically effective dose." Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

In the methods of the invention, the agents are administered as a short course of therapy prior to transplantation. Usually the treatment is completed at least about one week prior to transplantation, at least about 5 days prior to transplantation, at least about 3 days prior to transplantation. The process may be repeated if necessary, e.g. may be repeated twice, three times, four times, five times, or more, as necessary to clear the niche.

Conditions for Treatment

The indications for stem cell transplantation vary according to disease categories and are influenced by factors such as cytogenetic abnormalities, response to prior therapy, patient age and performance status, disease status (remission vs relapse), disease-specific prognostic factors, availability of a suitable graft source, time of referral, and time to transplant.

Autologous HSCT is currently used to treat the following conditions: Multiple myeloma, Non-Hodgkin lymphoma, Hodgkin disease, Acute myeloid leukemia, Neuroblastoma, Germ cell tumors, Autoimmune disorders—Systemic lupus erythematosus (SLE), systemic sclerosis, Amyloidosis.

Allogenic HSCT is currently used to treat the following disorders: Acute myeloid leukemia, Acute lymphoblastic leukemia, Chronic myeloid leukemia; Chronic lymphocytic leukemia, Myeloproliferative disorders, Myelodysplastic syndromes, Multiple myeloma, Non-Hodgkin lymphoma, Hodgkin disease, Aplastic anemia, Pure red cell aplasia, Paroxysmal nocturnal hemoglobinuria, Fanconi anemia, Thalassemia major, Sickle cell anemia, Severe combined immunodeficiency (SCID), Wiskott-Aldrich syndrome, Hemophagocytic lymphohistiocytosis (HLH), Inborn errors of metabolism—Eg, mucopolysaccharidosis, Gaucher disease, metachromatic leukodystrophies, and adrenoleukodystrophies, Epidermolysis bullosa, Severe congenital neutropenia, Shwachman-Diamond syndrome, Diamond-Blackfan anemia, Leukocyte adhesion deficiency, and the like.

Embodiments of the invention include transplantation into a patient suffering from a genetic blood disorder, where exogenous stem cells of a normal phenotype are transplanted into the patient. Such diseases include, without limitation, the treatment of anemias caused by defective hemoglobin synthesis (hemoglobinopathies). The stem cells may be allogeneic stem cells of a normal phenotype, or may be autologous cells that have been genetically engineered to delete undesirable genetic sequences, and/or to introduce genetic sequences that correct the genetic defect.

Sickle cell diseases include HbS Disease; drepanocytic anemia; meniscocytosis. Chronic hemolytic anemia occurring almost exclusively in blacks and characterized by sickle-shaped RBCs caused by homozygous inheritance of Hb S. Homozygotes have sickle cell anemia; heterozygotes are not anemic, but the sickling trait (sicklemia) can be demonstrated in vitro. In Hb S, valine is substituted for glutamic acid in the sixth amino acid of the beta chain. Deoxy-Hb S is much less soluble than deoxy-Hb A; it forms a semisolid gel of rodlike tactoids that cause RBCs to sickle at sites of low $PO_2$. Distorted, inflexible RBCs adhere to vascular endothelium and plug small arterioles and capillaries, which leads to occlusion and infarction. Because sickled RBCs are too fragile to withstand the mechanical trauma of circulation, hemolysis occurs after they enter the circulation. In homozygotes, clinical manifestations are caused by anemia and vaso-occlusive events resulting in tissue ischemia and infarction. Growth and development are impaired, and susceptibility to infection increases. Anemia is usually severe but varies highly among patients. Anemia may be exacerbated in children by acute sequestration of sickled cells in the spleen.

Thalassemias are a group of chronic, inherited, microcytic anemias characterized by defective Hb synthesis and ineffective erythropoiesis, particularly common in persons of Mediterranean, African, and Southeast Asian ancestry. Thalassemia is among the most common inherited hemolytic disorders. It results from unbalanced Hb synthesis caused by decreased production of at least one globin polypeptide chain ($\beta$, $\alpha$, $\gamma$, $\delta$).

Aplastic anemia results from a loss of RBC precursors, either from a defect in stem cell pool or an injury to the microenvironment that supports the marrow, and often with borderline high MCV values. The term aplastic anemia commonly implies a panhypoplasia of the marrow with associated leukopenia and thrombocytopenia.

Combined immunodeficiency is a group of disorders characterized by congenital and usually hereditary deficiency of both B- and T-cell systems, lymphoid aplasia, and thymic dysplasia. The combined immunodeficiencies include severe combined immunodeficiency, Swiss agammaglobulinemia, combined immunodeficiency with adenosine deaminase or nucleoside phosphorylase deficiency, and combined immunodeficiency with immunoglobulins (Nezelof syndrome). Most patients have an early onset of infection with thrush, pneumonia, and diarrhea. If left untreated, most die before age 2. Most patients have profound deficiency of B cells and immunoglobulin. The following are characteristic: lymphopenia, low or absent T-cell levels, poor proliferative response to mitogens, cutaneous anergy, an absent thymic shadow, and diminished lymphoid tissue. *Pneumocystis* pneumonia and other opportunistic infections are common.

EXPERIMENTAL

Example 1

A Non-Genotoxic Conditioning Regimen for Haploidentical Hematopoietic Stem Cell Transplantation Materials and Methods Mice. All donor and recipient mice were between 8 and 12 weeks of age. Donor mice were AKR× Hz F1 mice bred by the Shizuru lab. AKR×Hz F1 mice are double positive for 45.1 and 45.2, and H2Kb and H2Kk. Recipient mice were CB6F1 from JAX. CB6F1 mice are single positive for 45.2 and double positive for H2Kb and H2Kd. All procedures were approved by the International Animal Care and Use Committee. Mouse strains were maintained at Stanford University's Research Animal Facility.

Antibodies. All antibodies for in vivo conditioning were purchased from Bio X Cell, including anti-CD47 (clone 3/clone mIAP410), anti-CD117 (clone ACK2), anti-CD40L (clone MR-1), and anti-CD122 (clone TM-b1).

BM Transplant. Recipient CB6F1 mice were given a priming dose of 100ug of anti-CD47 intraperitoneally on Day −8. On Day −6, mice were given a 500ug retro-orbital injection of anti-CD117. Prior to anti-CD117 treatment, mice were given an intraperitoneal injection of Benadryl. On Days −6 through −2, mice were also given 500ug daily intraperitoneal injections of anti-CD47. On Day −2, mice were given up to 250ug of anti-CD122. On Day 0, 500ug of anti-CD40L is given a few hours prior to transplantation.

For transplantation, whole bone marrow is harvested from 8-12 week old AKR×Hz mice. The whole bone marrow is taken from tibia, femurs, hips, and spine. The red blood cells are lysed and the remaining cells are counted and appropriately resuspended prior to injection. The cells are delivered with a retro-orbital injection.

Chimerism checks. Recipient mice are periodically bled with a retro-orbital puncture to measure donor chimerism. The blood is stained with fluorescent antibodies against CD45.1, CD45.2, CD3, CD19, CD11b, and Gr-1.

Results

As shown in FIGS. 1A-1F, a combination of antibodies specific for c-kit, CD47, CD40L and CD122, with the protocol described above, enabled efficient engraftment of haploidentical whole bone marrow into immune competent animals. Shown in FIG. 2 are the percentage of mice that were chimeric per cohort and the average levels of total donor, T-cell, B-cell, and granulocyte chimerism. At low doses of cells, as shown in FIG. 3, NK cel depletion with anti-CD122 is required.

Example 2

Antibody Conditioning Enables MHC-Mismatched Hematopoietic Stem Cell Transplants and Organ Graft Tolerance Replacing a patient's diseased blood system by hematopoietic cell transplantation (HCT) can treat or cure genetic disorders of the blood and immune system, including leukemia, autoimmune diseases and immunodeficiencies. In HCT, a patient's blood and immune systems are typically ablated using toxic "conditioning regimens" (chemotherapy and/or radiation) and then replaced with donor cells containing hematopoietic stem cells (HSCs) to regenerate a healthy blood system. While HCT is a foundational treatment, its use and safety are hindered by graft vs. host disease (which can be overcome by transplanting purified HSCs devoid of contaminating donor T cells) and lethal toxicities caused by the conditioning regimens. Therefore, a decisive goal is to achieve HCT conditioning with more specific, safer agents (e.g., monoclonal antibodies), obviating the need for toxic chemotherapy or radiation.

Here we show that a combination of six monoclonal antibodies can safely and specifically deplete host HSCs, T cells and NK cells of immune-competent mice and permit foreign (allogeneic) HSC engraftment. The engrafted donor HSCs were either mismatched at half (haploidentical) or all the MHC genes, and in both cases generated donor blood and immune systems that stably co-exist with host blood cells. These chimeric immune systems were functional, as exhibited by tolerance to HSC donor strain heart tissue and rejection of $3^{rd}$ party hearts. These studies demonstrate antibody conditioning, which can be applied to purified human HSC transplantation as a platform for regenerative medicine, facilitating applications including foreign organ transplants and treatment of diverse blood and immune system disorders.

A multitude of genetic blood and immune system disorders can be treated by hematopoietic cell transplantation (HCT): examples include thalassemia, sickle cell anemia, Fanconi's anemia, inherited immunodeficiencies, autoimmune diseases (e.g., multiple sclerosis), and metabolic storage disorders. These diseases can be corrected when an individual's blood system is replaced by healthy, transplanted blood cells, which stably derive from the transplanted rare hematopoietic stem cells (HSCs) in HCT grafts. After regeneration of a donor-derived blood and immune system, HCT recipients are immunologically tolerant to organ transplants from the HSC donor. While any single-gene or multi-gene genetic disorder of the blood system could be cured by allogeneic HCT, treatment of non-malignant hematological or immunological disorders only accounted for 6% of total HCT cases reported in Europe in 2015.

To overcome the disproportionately infrequent use of HCT to treat non-malignant blood disorders and extend its reach, two key challenges must be addressed: safety concerns and donor availability. At present, allogeneic HCT leads to clinical or subclinical graft vs. host disease (GvHD) caused by contaminating donor-derived T cells; but GvHD can be overcome by transplanting purified HSCs devoid of T cells. Moreover, HCT conditioning requires chemotherapy and radiation, which can induce life-threatening side effects.

Another challenge confronting HCT for genetic blood disorders is the current need for fully matched donors at the human leukocyte antigen (HLA, otherwise known as major histocompatibility complex [MHC]) loci; while 75% of Caucasian Americans currently have matched donors, it is markedly harder to find fully-matched donors for Black Americans (16-19% currently have a match) or other underrepresented ethnic groups. If it were possible to safely perform HCT using haploidentical donors (which are matched at half of HLA loci), this would significantly expand the availability of donors to theoretically enable any individual to receive HCT from their parent, child, or 75% of siblings. Finally, if it were possible to safely transplant fully HLA-mismatched HSCs, this would massively open the pool of available donors; with the added benefit that recipients would be immunologically tolerant to foreign organs or tissues obtained from the same donor. This would enable HLA-mismatched organ transplants without the lifelong immunosuppression commonly needed to prevent rejection for vital organ transplants.

The safety of HCT would be considerably improved if toxic conditioning regimens (chemotherapy and/or radiation) were replaced by more specific agents, such as monoclonal antibodies depleting components of the immune system. While prior antibody conditioning regimens enable the transplantation of minor histocompatibility antigen-mismatched HSCs (see, for example, patent publication WO 2016/033201), transplantation of MHC-mismatched HSCs using antibody-based conditioning has not previously been shown.

Here we demonstrate that conditioning using six monoclonal antibodies enables wild-type mice to receive partially- (haploidentical) or fully-MHC mismatched HSCs, therefore enabling blood system replacement and induction of tolerance to mismatched donor organs without recourse to chemotherapy or radiation.

Figure 4A:
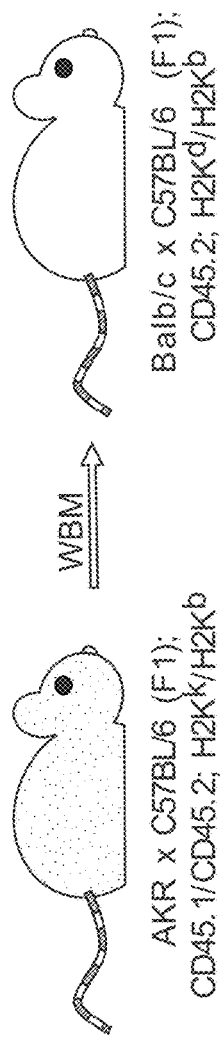
Figure 4B:
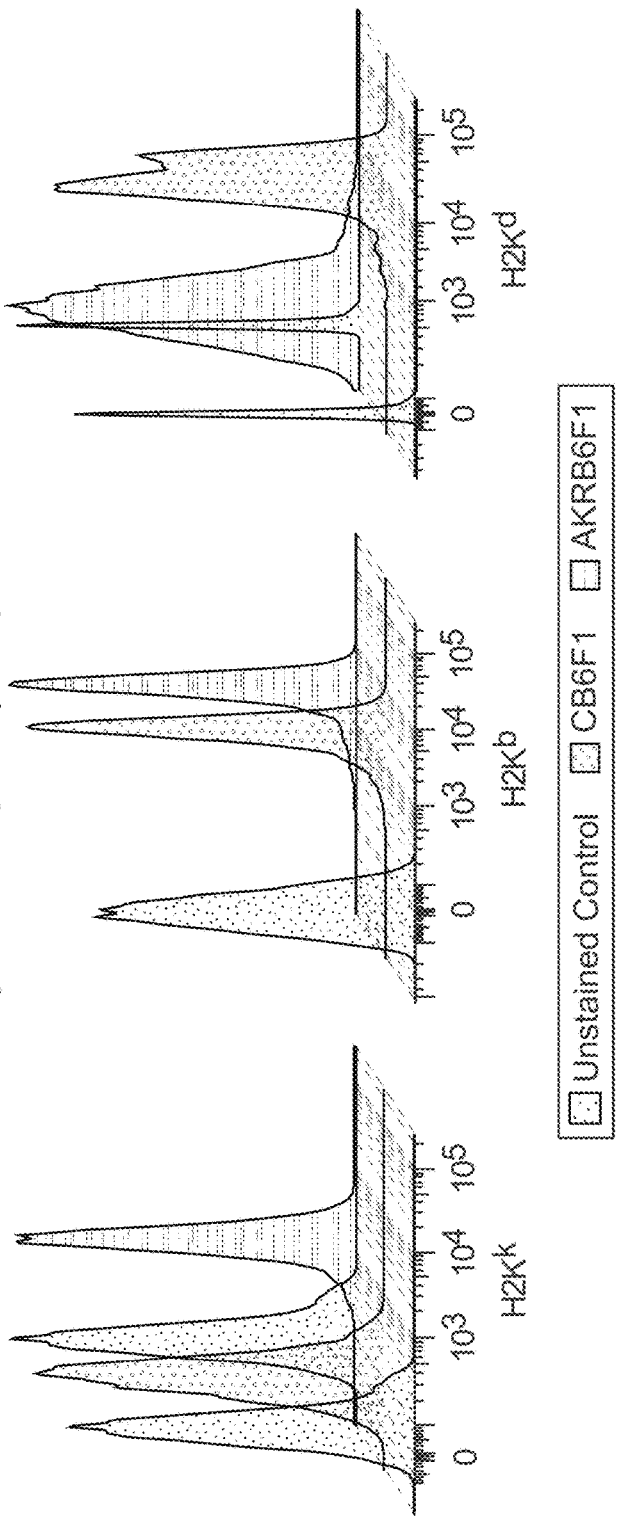

For haploidentical transplantation experiments, AKR× C57BL/6 $F_1$ (hereafter referred to as $AB6F_1$) mice were used as bone marrow or HSC donors and BALB/C λ C57BL/6 $F_1$ ($CB6F_1$) (FIG. 4a) mice served as recipients; these mouse strains are only matched at the $H2^b$ haplotype but mismatched for $H2^k$ and $H2^d$ (i.e., at half of the Major Histocompatibility Complex [MHC] haplotypes) (FIG. 4b). We sought to determine if conventional conditioning could be replaced with monoclonal antibodies (mAb). We previously demonstrated that immune-deficient mice could be conditioned using an anti-Kit antibody to enable syngeneic HSC engraftment, whereas comparable conditioning of immune-competent mice required dual administration of anti-Kit and anti-CD47 blocking agents. CD47 blockade enables macrophages to phagocytose antibody-bound (opsonized) cells, such as $KIT^+$ HSCs opsonized by anti-c-KIT antibodies.

In order to engraft allogeneic HSCs mismatched at the MHC loci, it may require suppressing or eliminating both T cells and NK cells, which reject cells expressing foreign major and minor histocompatibility antigens or that lack "self" MHC. To eliminate host NK cells we targeted CD122/ Il2Rβ (which is expressed throughout human and mouse NK cell development) using the anti-CD122 mAb Tm-β1 to deplete these cells. To prevent T-cell mediated rejection we targeted CD40L (also known as CD154), which is a co-stimulatory cell surface molecule expressed by activated T-cells and is required for their signaling with $CD40^+$ antigen presenting cells. Interruption of the CD40-CD40L axis can help induce tolerance to hematopoietic cells and skin grafts and importantly, does not deplete all T cells since CD40L is upregulated on activated T cells; we inhibited CD40L using the anti-CD40L antibody MR1.

Figure 4C:
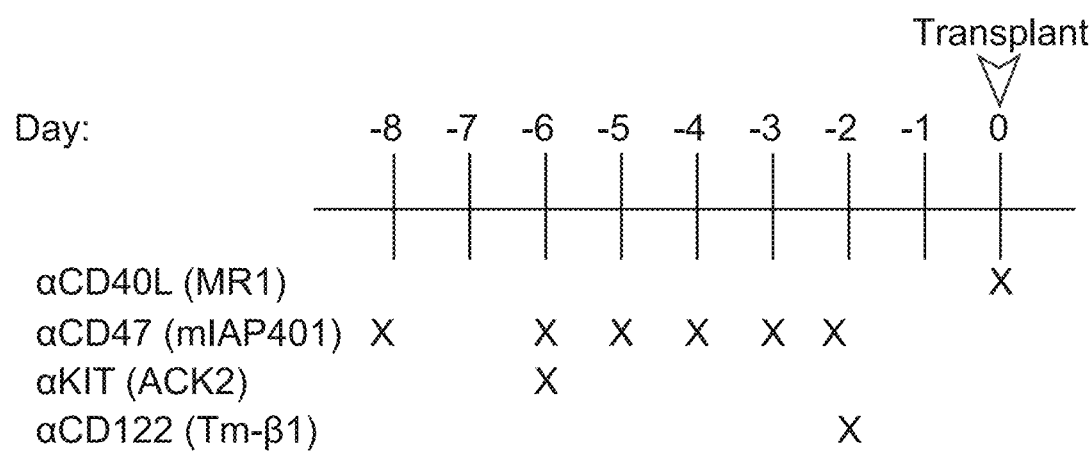
Figure 4D:
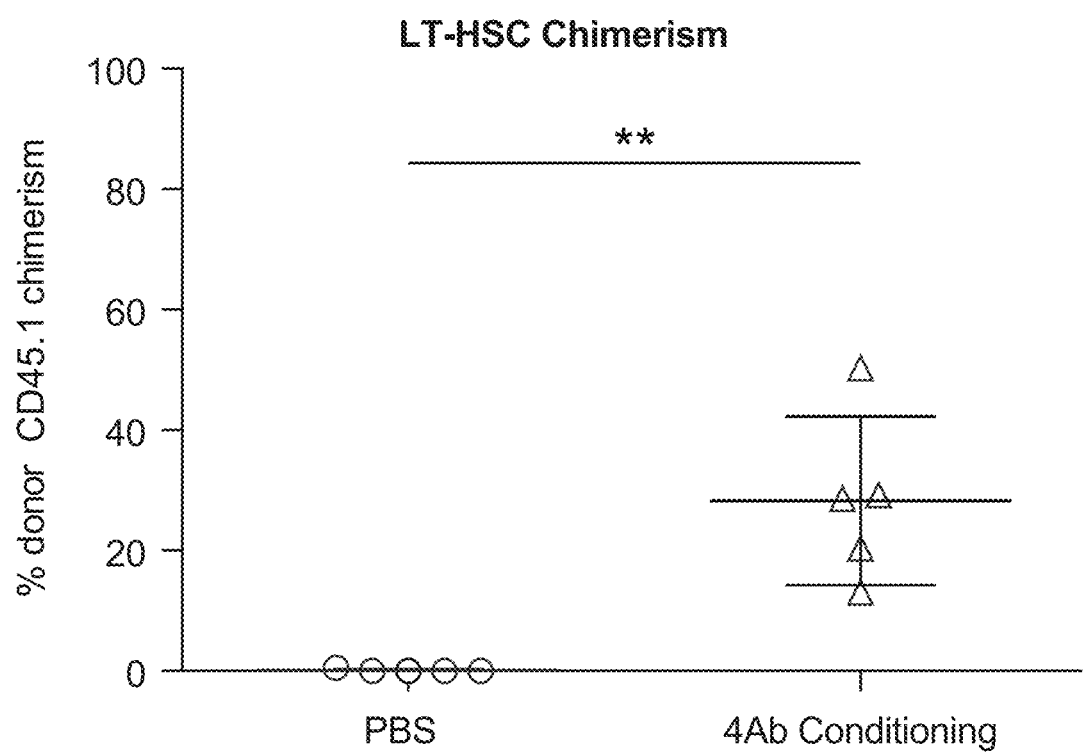
Figure 8A:
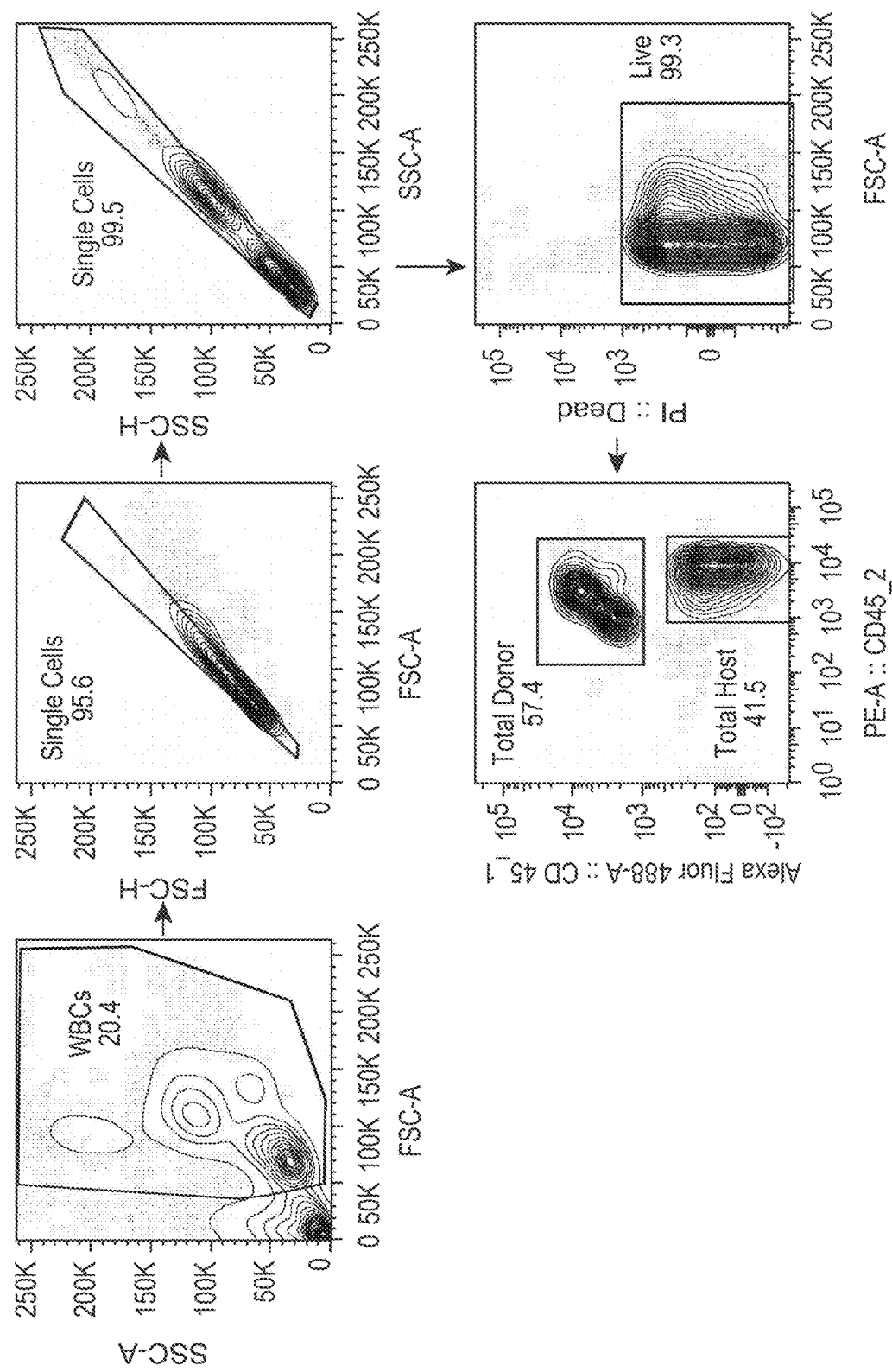
FIG. 8A-8D.
Figure 8B:
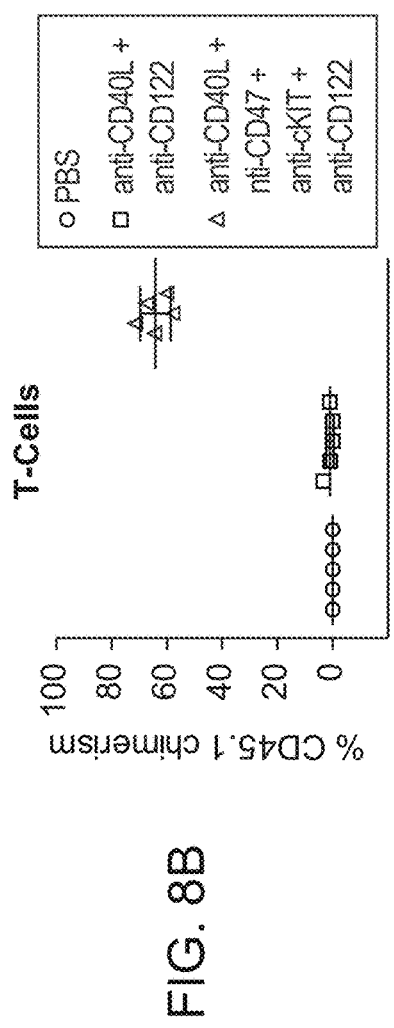
Figure 8D:
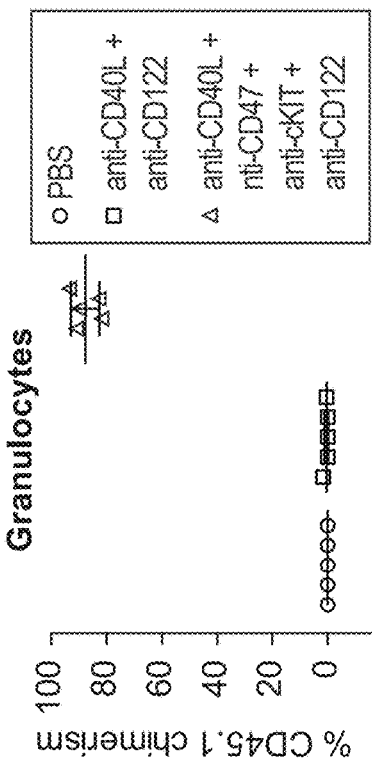
Figure 8C:
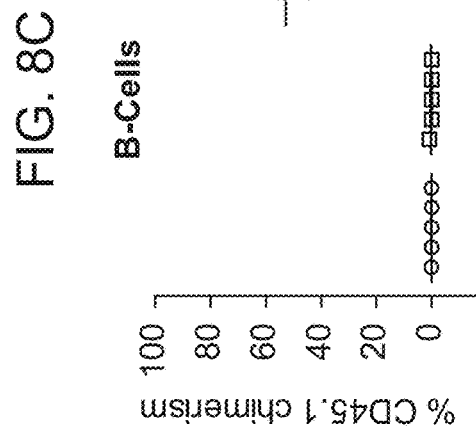

Mice were treated over the course of eight days (FIG. 4c) with the four monoclonal antibodies (anti-CD122, anti-CD40L, anti-Kit and anti-CD47; herein referred to as 4Ab conditioning) and then transplanted with 30 million whole bone marrow (WBM) cells. Chimerism was periodically measured by CD45 allelic differences (FIG. 8a) and multi-lineage mixed chimerism was observed in all animals receiving 4Ab conditioning (FIG. 8b-d). Importantly, mixed chimerism was also observed in the long-term HSC (LT-HSC) compartment (FIG. 4d), indicating that the donor chimerism did not result from engraftment of long-lived mature immune cells, but was being actively maintained by donor stem cells.

Figure 4G:
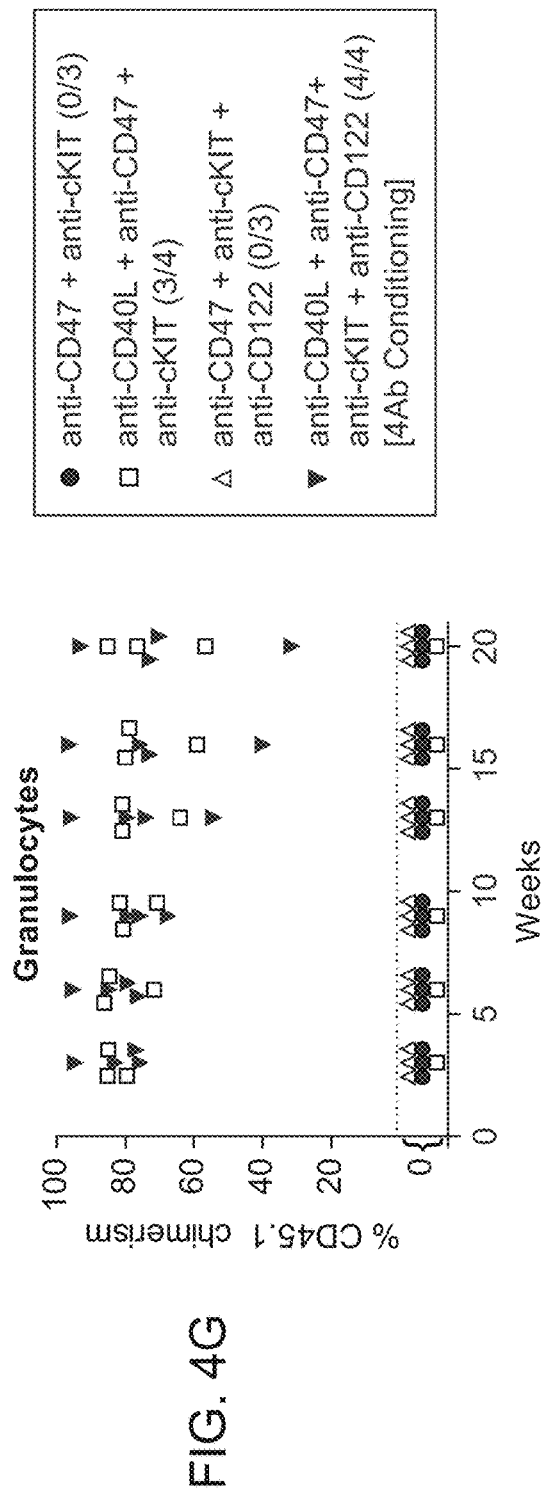
Figure 4H:
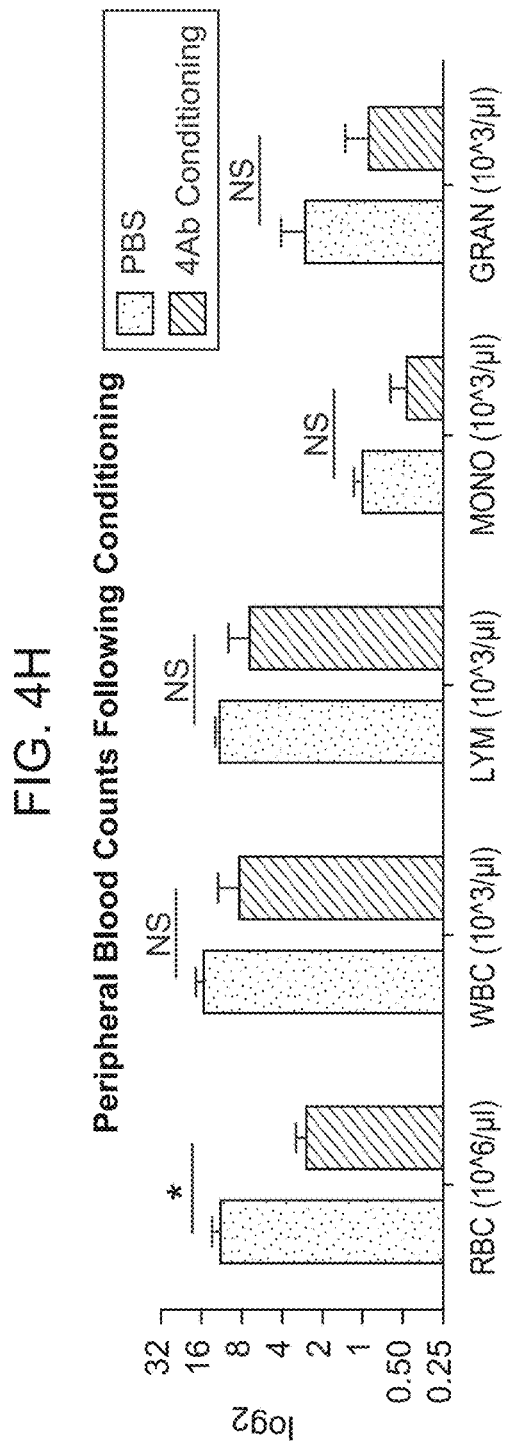

To identify the minimally necessary components of this cocktail, we tested each antibody in isolation (FIG. 9) and then as various combinations of the four antibodies. The minimally necessary cocktail for 30 million WBM cells to engraft was anti-CD47, anti-c-KIT, and anti-CD40L (FIG. 4e-g). However, only 75% of the mice in the group lacking anti-CD122 were chimeric. In the group receiving the complete 4Ab conditioning, 100% of the mice were chimeric. Interestingly, engrafted animals from both groups showed similar levels of multi-lineage chimerism over twenty weeks. Additionally, the 4Ab conditioning did not induce granulocytopenia prior to transplantation (FIG. 4h).

Figure 4I:
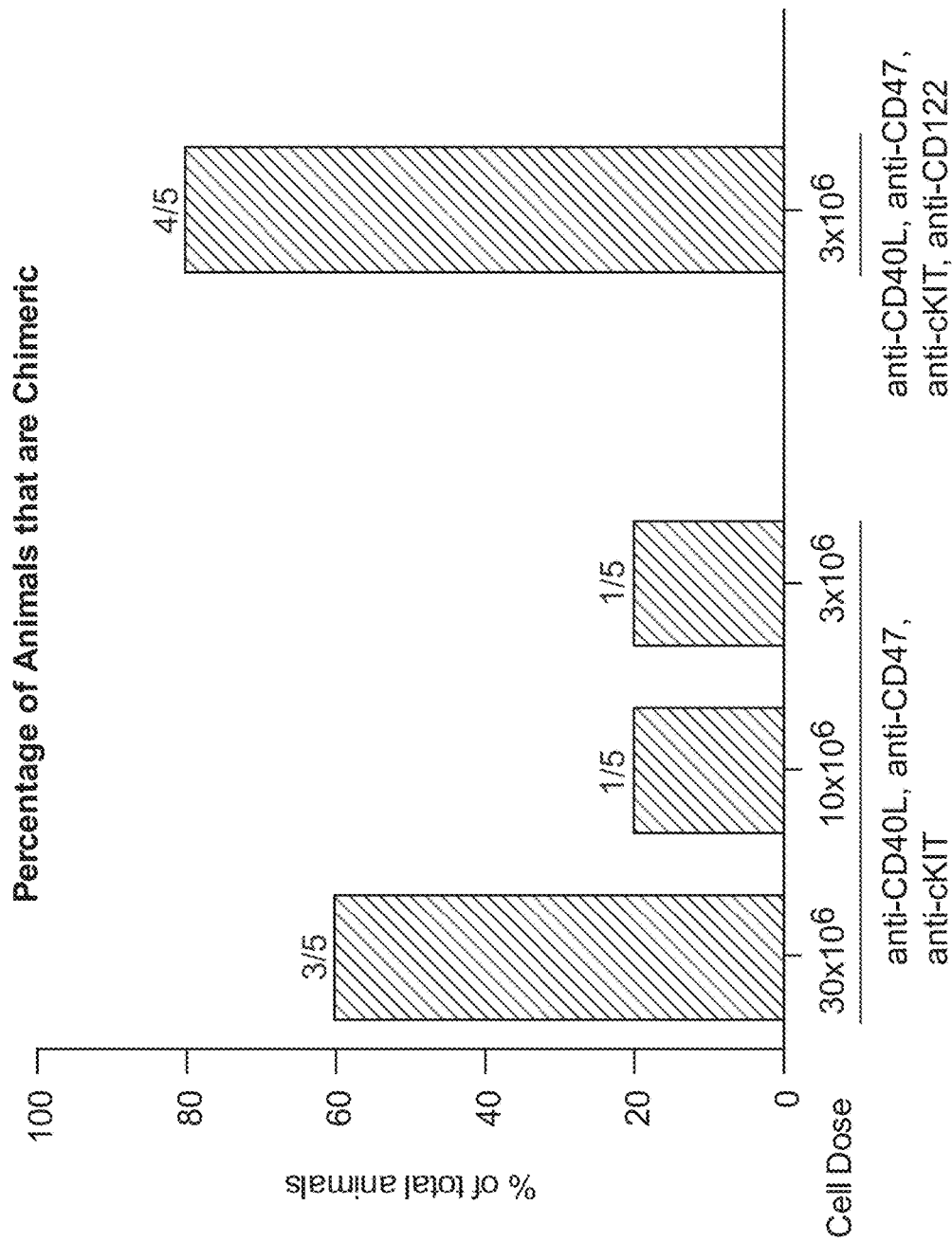

We tested the lowest dose of WBM that could engraft by titrating the dose of WBM while modulating the usage of anti-CD122. The number of chimeric mice decreased as the amount of bone marrow transplanted decreased (FIG. 4i). At 3 million WBM cells, 20% of mice were chimeric without anti-CD122, while 80% of mice were chimeric in this cell dose group with NK depletion.

Figure 5A:
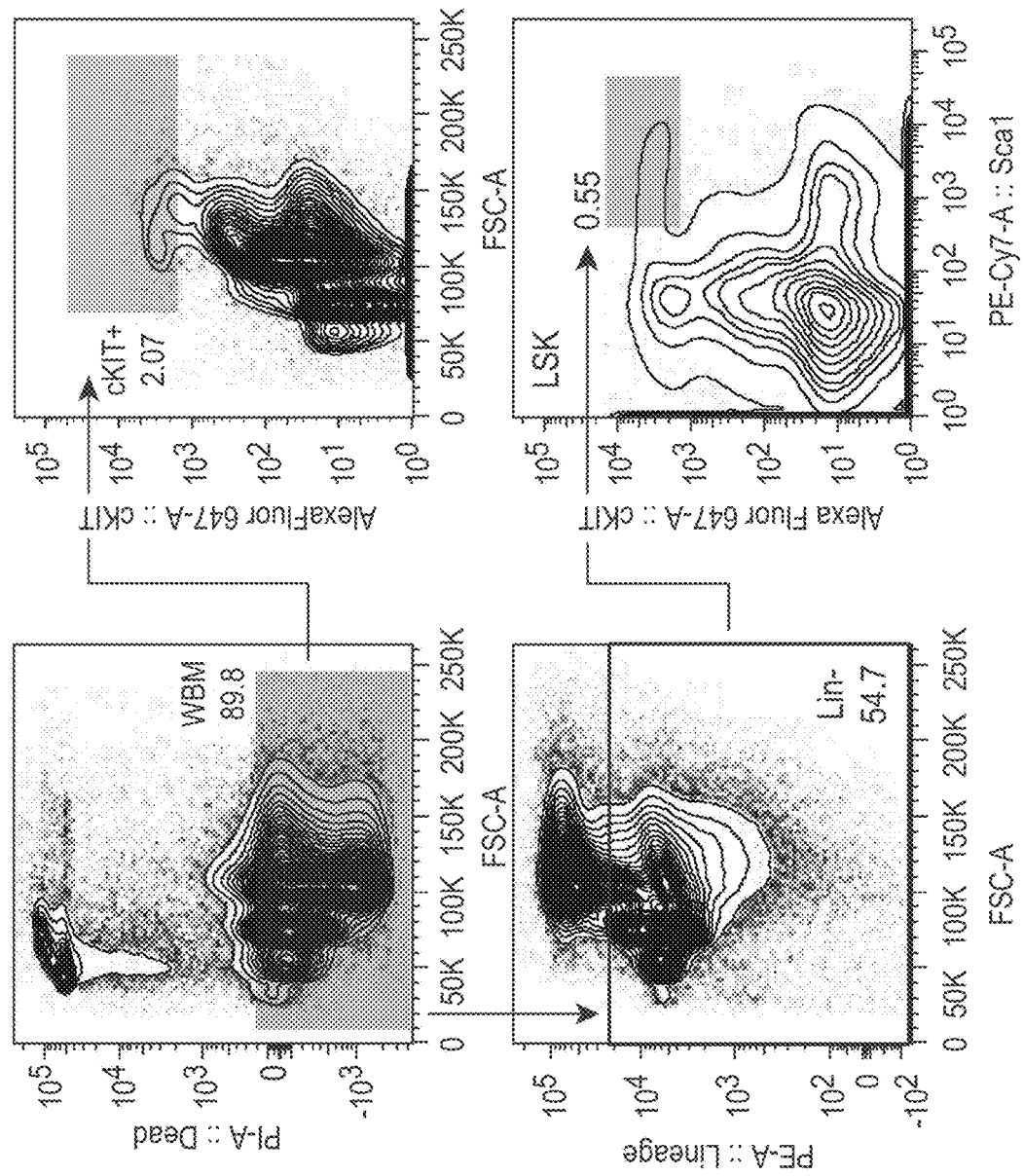
Figure 5B:
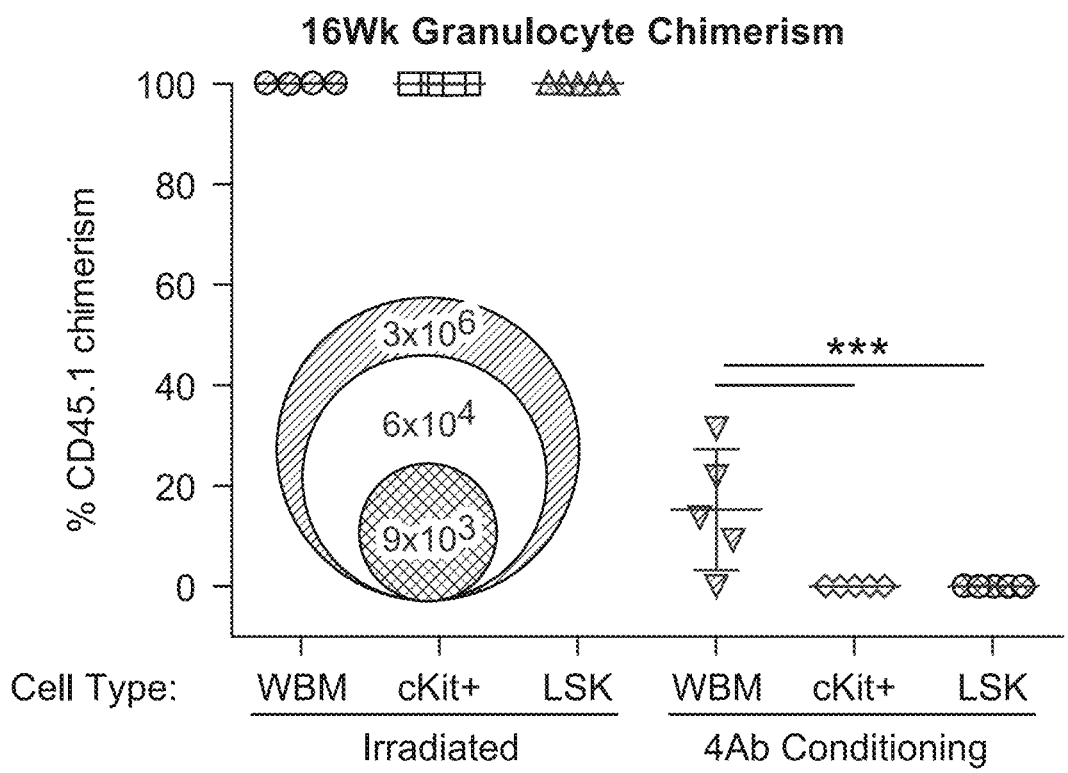

To eliminate the possibility of GvHD, next we transplanted enriched HSC populations (as opposed to WBM). In these experiments Lineage$^-$ Sca1$^+$ Kit$^+$ (LSK) cells (FIG. 5a) were transplanted, which are highly enriched for HSC and multipotent progenitor (MPP) cells. Both Kit enriched and LSK cells were given in quantities that corresponded to their abundance in 30 million WBM cells (FIG. 5b). All three types of grafts showed complete, long-term multi-lineage chimerism in irradiated controls. Strikingly, while 4Ab-conditioned mice were successfully engrafted long term by WBM, they were not reconstituted by Kit-enriched or LSK transplants (FIG. 5b). This therefore indicates that additional conditioning antibodies may be required for enriched HSC populations to successfully engraft.

Figure 5C:
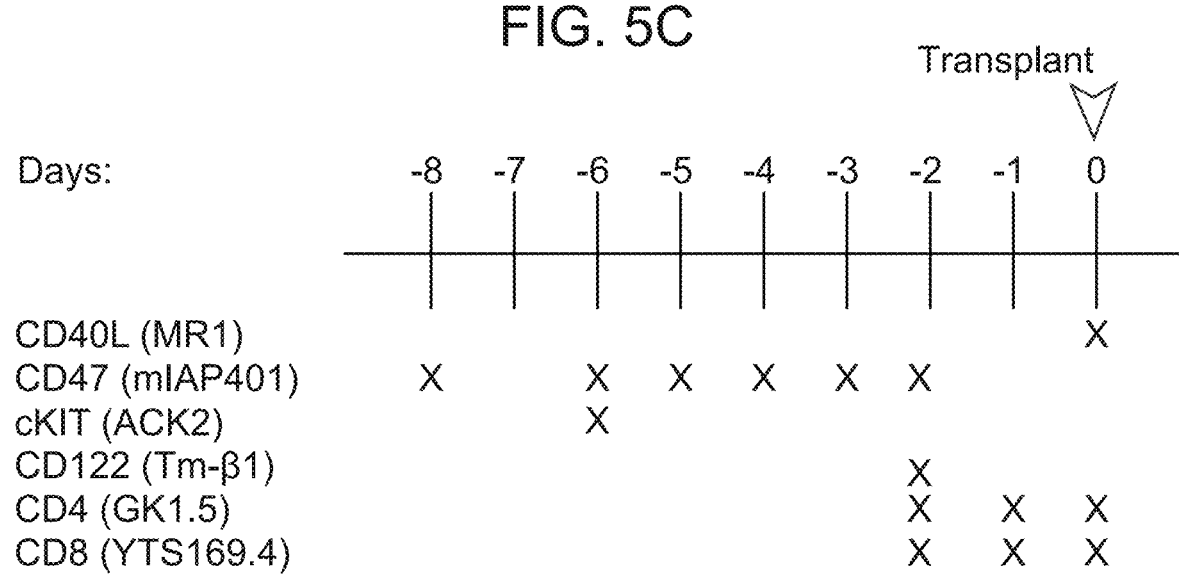
Figure 5E:
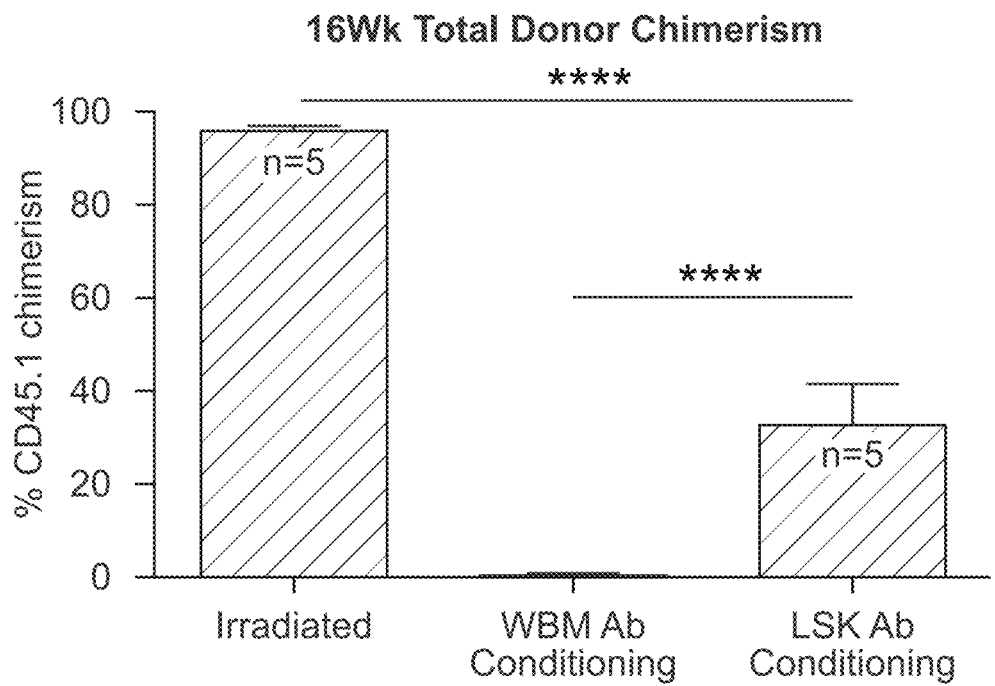
Figure 10A:
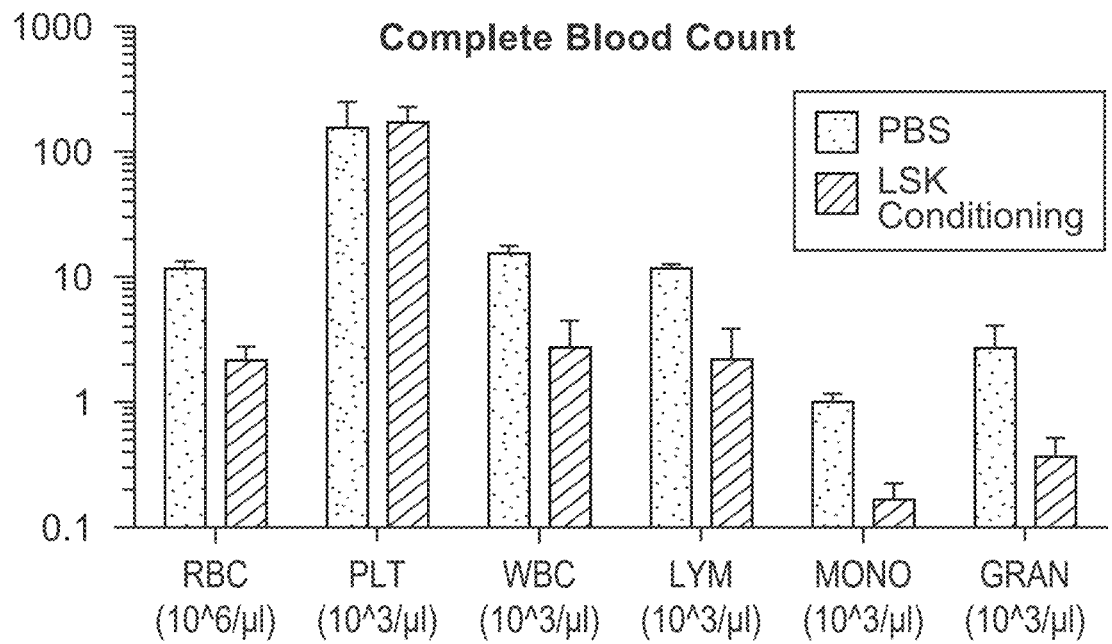
FIG. 10A-10C. Complete blood count FIG. 10A, peripheral blood subpopulations FIG. 10B and splenic subpopulations FIG. 10C from animals one day after conditioning is completed without transplantation.
Figure 10B:
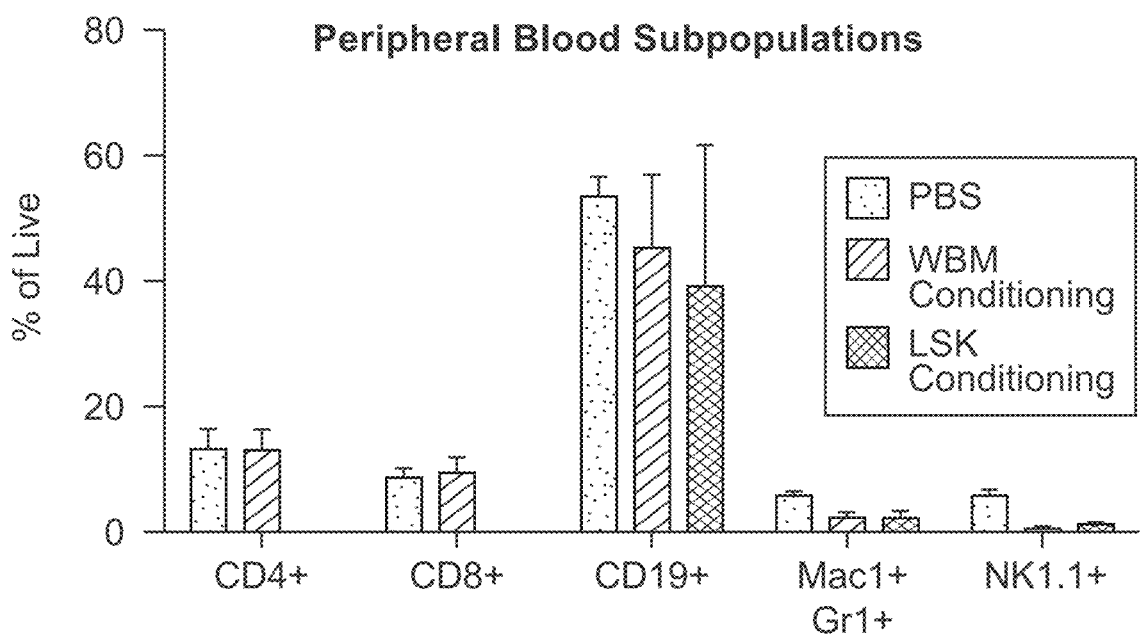
Figure 10C:
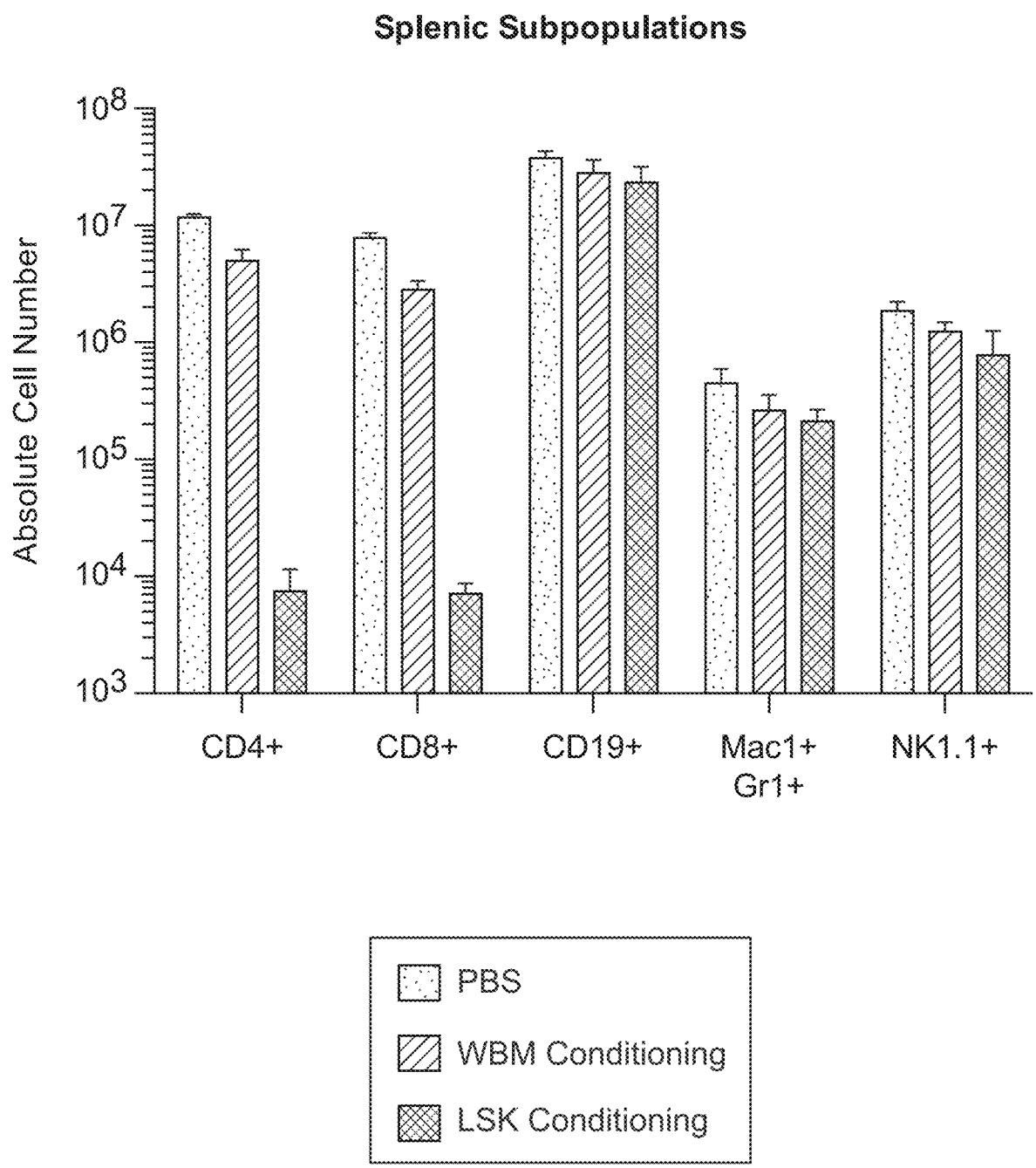

In order to facilitate LSK engraftment we attempted to provide additional immune suppression by eliminating T cells using anti-CD4 and anti-CD8 depleting antibodies (FIG. 5c). The addition of anti-CD4 and anti-CD8 antibodies to the 4Ab regime robustly depleted T-cells from peripheral blood, spleen and bone marrow (FIG. 5d and FIG. 10). The usage of this six antibody cocktail, which will be referred to as 6Ab conditioning (anti-CD122, anti-CD40L, anti-Kit, anti-CD47, anti-CD4 and anti-CD8 mAbs), induced long term chimerism in recipients transplanted with 9000 LSK cells (FIG. 5e). This cell dosage corresponds to approximately 360,000 LSK/kg, which is well below HSC doses seen in preclinical testing for allografts in mice and clinical usage in autografts in humans. In summary, 6Ab conditioning enables low doses of cells, e.g. purified HSC, to engraft mice without recourse to chemotherapy or radiation.

Figure 5F:
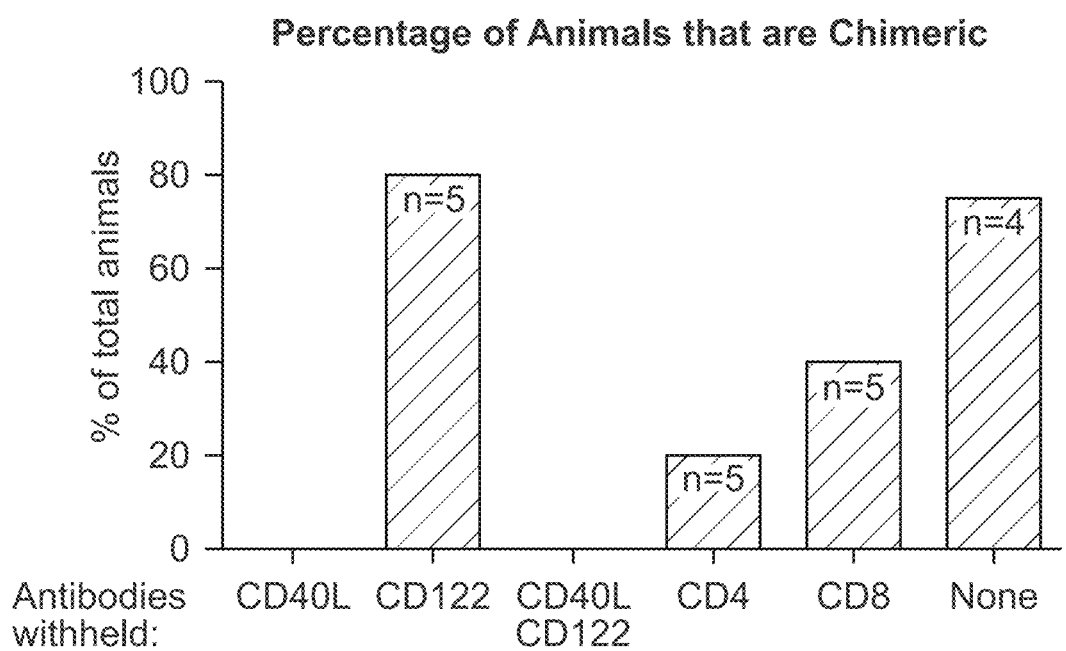

To determine if all six components of this cocktail were necessary, we used a reductive process to identify the dispensable antibodies. Removal of anti-CD40L, anti-CD4, and anti-CD8 resulted in fewer chimeric animals and lower chimerism within each cohort, as compared to the complete 6Ab conditioning cohort (FIG. 5f and FIG. 11). However, removal of the anti-CD122 antibody did not significantly change the percentage of chimeric animals as compared to the control cohort. Unlike in the 4Ab conditioning regimen, CD122 may be less necessary in the 6Ab conditioning due to NK dependence on T-cell activation, which is lost in the 6Ab conditioning regimen, as there is near complete depletion of T-cells.

Figure 6A:
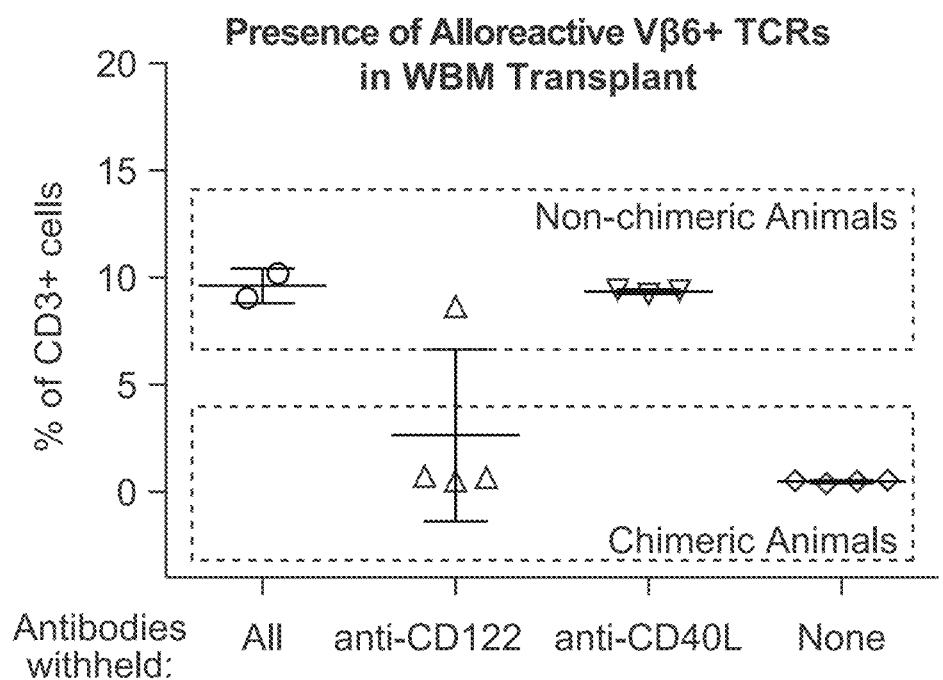
FIG. 6A-6E. Low dose LSK transplantation via a non-genotoxic conditioning regimen allows for tolerance to donor tissue.
Figure 6B:
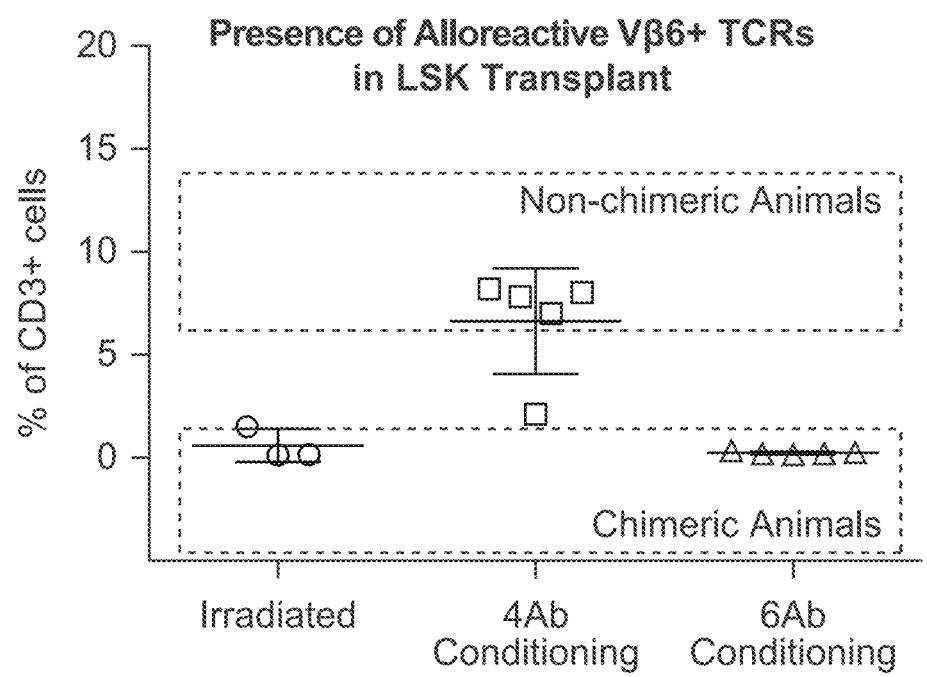

Importantly, 6Ab conditioning followed by HSC transplantation induced centrally-mediated immunological tolerance to the donor genetic strain. Central tolerance implies thymic re-education of the host immune system to permit donor cell engraftment. To gauge central tolerance in these animals, we measured the presence of the V beta 6 (Vb6) TCR chain in peripheral blood. The Vb6 is reactive to the Mtv-7 provirus-encoding super-antigen, which is present in the AKR strain. Therefore, for AB6F$_1$ HSCs to coexist in CB6F$_1$, the CB6F$_1$ endogenous Vb6+ T-cells must be clonally deleted. In both WBM- and LSK-transplanted animals, chimeric animals showed deletion of host Vb6+ T-cells (FIG. 6a-b). Interestingly, in the WBM cohort conditioned with anti-Kit, anti-CD47, and anti-CD40L, the only animal with a normal Vb6+ T-cell frequency also never achieved chimerism (FIG. 6b).

Figure 6C:
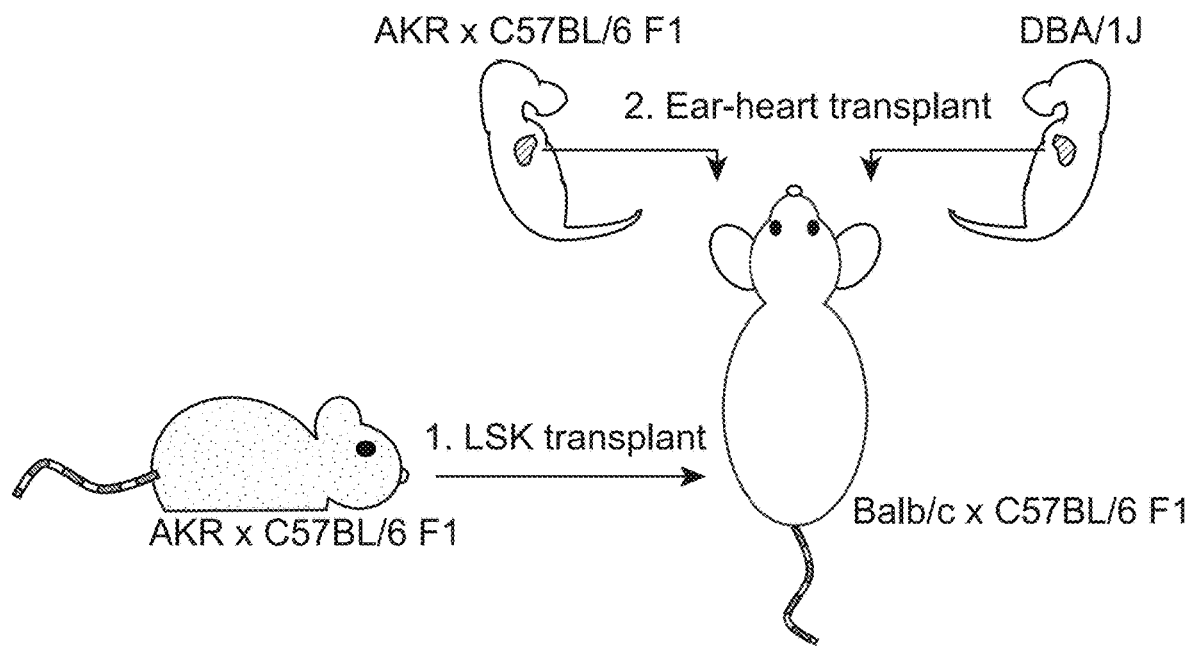
Figure 6D:
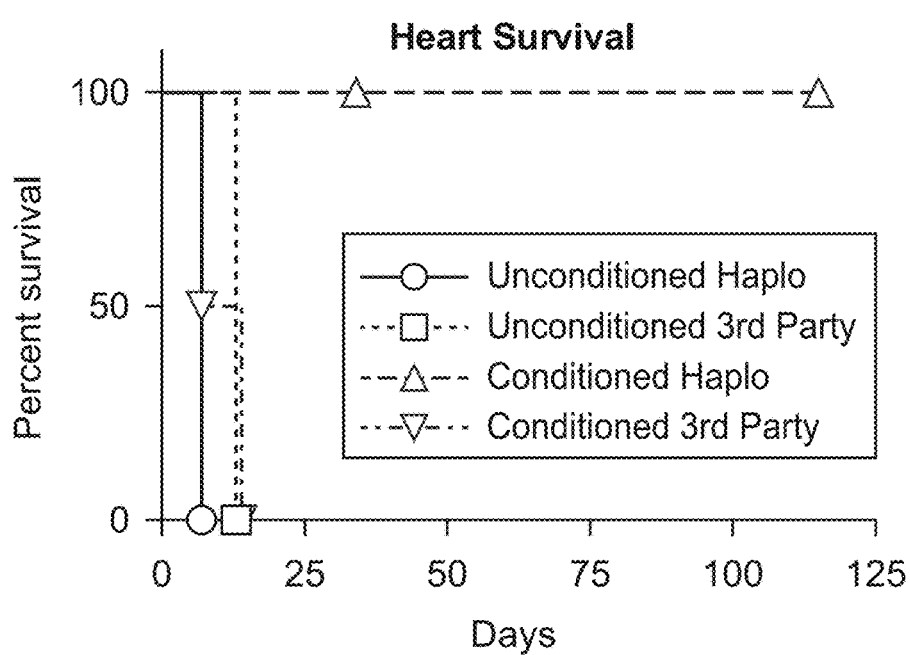
Figure 6E:
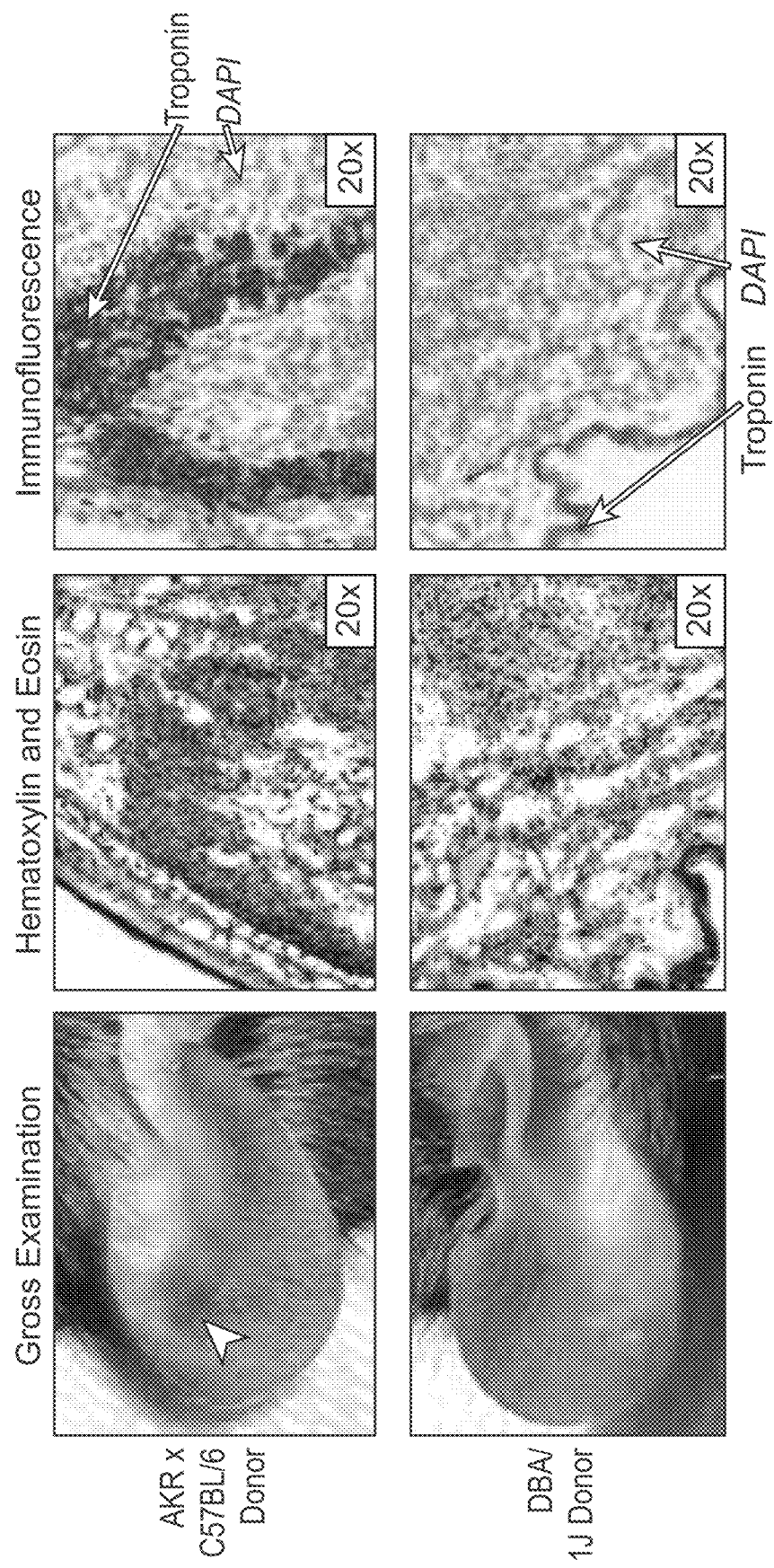

Strikingly, we found that 6Ab-conditioned mice engrafted with MHC-mismatched donor HSC were immunologically tolerant to organs from the same donor strain. To this end, we transplanted heart grafts from HSC donor (AB6F$_1$) or third-party (DBA1/J strain, which are homozygous for H2$^q$) newborn pups into the ear pinna of naïve and LSK-Ab conditioned chimeric animals (FIG. 6c). In naïve, unconditioned, untransplanted mice, both AB6F$_1$ and DBA1/J hearts were rejected rapidly (FIG. 6d). In 6Ab conditioned chimeric mice, DBA1/J hearts were rejected within 14 days while active, beating AB6F1 hearts persisted for at least 115 days. Representative ear-heart grafts were harvested at 34 days and analyzed by immunohistochemistry. Upon gross examination, AB6F1 hearts are visible in the pinna while DBA/1J hearts are no longer apparent (FIG. 6e). H&E analysis showed troponin+ cardiac tissue lacking immune cell infiltrates in the AB6F1-engrafted pinna; however, by this time there was no cardiac or troponin+ tissue within the pinna containing DBA/1J hearts (FIG. 6e). This therefore indicates that MHC-mismatched donor HSC can induce immunological tolerance of 6Ab-conditioned mice to heart grafts from the same genetic donor.

Figure 7A:
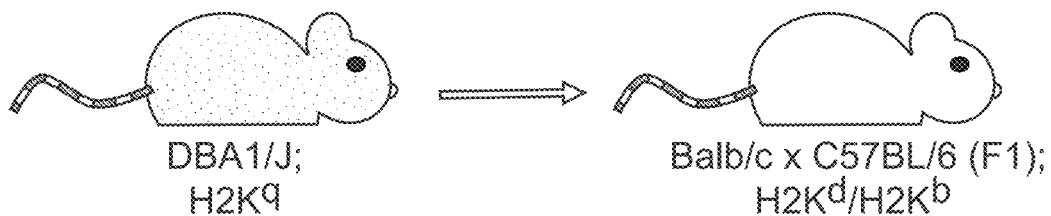
FIG. 7A-7D. Hematopoietic stem cells can be engrafted despite a full MHC mismatch.
Figure 7B:
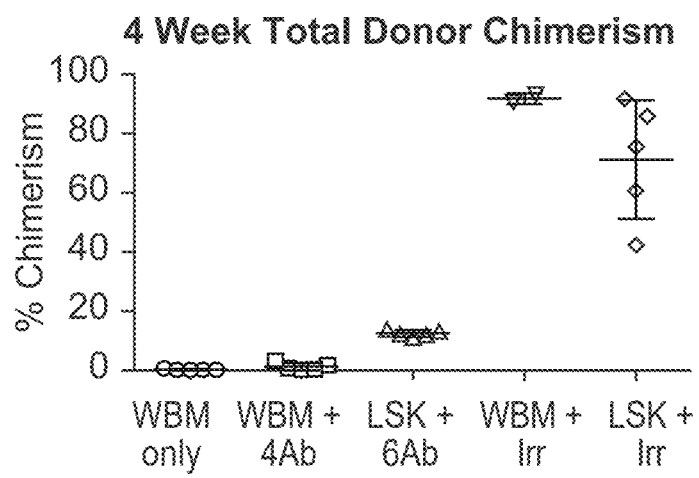
Figure 7C:
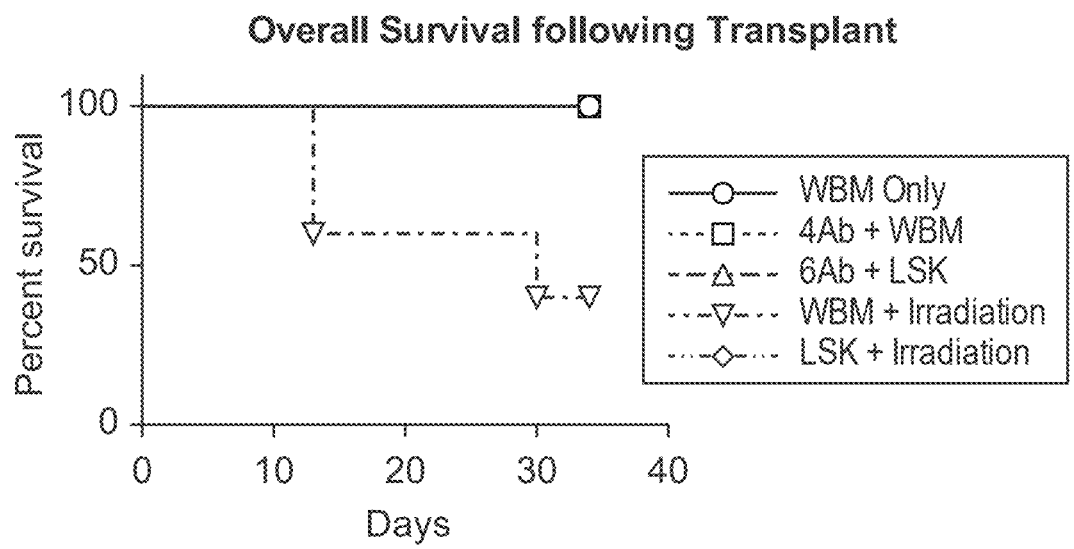
Figure 7D:
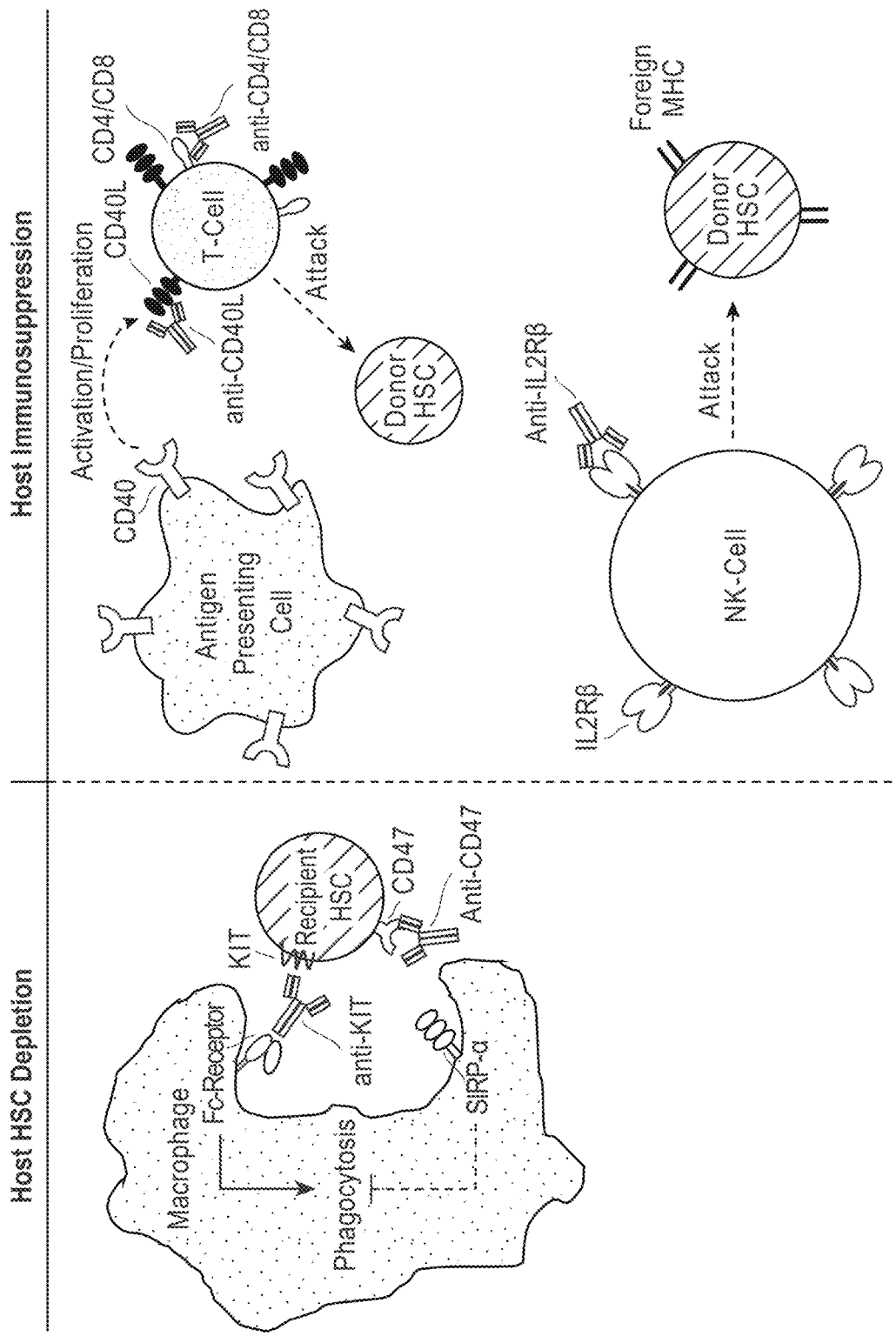

Finally, we demonstrated that the 6Ab conditioning regimen enabled successful engraftment of fully MHC-mismatched HSCs. We used DBA1/J (H2$^q$) mice as donors and CB6F$_1$ (H2$^{b/d}$) hosts (FIG. 7a). After transplanting 9000 DBA1/J LSK cells, we observed high donor-host chimerism by 8 weeks in all 6Ab-conditioned CB6F$_1$ mice (FIG. 7b). Mice transplanted with 3 million WBM cells alone failed to establish donor chimerism (confirming the necessity for conditioning), while 40% of 4Ab-conditioned mice receiving WBM achieved low levels of chimerism. 80% of the irradiated CB6F1 mice transplanted with WBM were dead by 9 weeks following transplantation (FIG. 7c), likely by GvHD, which was not observed in LSK transplants.

In sum, here we have developed a method to transplant half- (haploidentical) and fully-MHC mismatched hematopoietic cell compositions, including purified HSC, into immune-competent animals; importantly this is accomplished without the use of chemotherapy and/or radiation, and without the GvHD that occurs in most, if not all, other types of HCT transplants.

These findings are relevant to clinical use of hematopoietic cells transplantation, for example for the treatment of blood and immune system disorders. First, this antibody conditioning regimen-combined with purified HSC transplants-improves the safety of blood and immune system replacement by obviating the use of chemotherapy/radiation and by eliminating GvHD. Second, by facilitating transplantation of haploidentical, HLA-mismatched HSCs, this increases significantly the donor pool to enable most recipients to find a match, even if their age or clinical status had prevented HCT under previous protocols. For instance, patients with Fanconi's anemia are highly susceptible to DNA damage, and therefore, conventional transplant conditioning regimens pose a serious risk to this cohort.

Lastly, the ability to induce immunological tolerance to foreign organs opens opportunities for all patients requiring lifesaving organ transplants: specifically, it obviates the need for lifelong immune suppression for patients to receive foreign organ transplants. In particular, the immune systems in antibody-conditioned, donor HSC-transplanted animals are tolerant to donor (but not third-party) hearts. The coexistence of donor and host T cells in these partially-chimeric animals can provide MHC-restricted T cells for both donor and host tissues.

Today, a donor of an organ, tissue or HSC transplant is a living or recently deceased person. A goal of regenerative medicine is to differentiate a pluripotent (embryonic or induced pluripotent) stem cell line into HSCs and other needed tissue stem cells (such as those of the neural, bone and cartilage, or liver), either in vitro or in vivo within a large-animal host (such as a pig). This relieves the need for human beings to give up their HSCs and organs for others. Antibody conditioning, followed by co-transplantation of pluripotent stem cell-derived HSC and tissue stem cells, could deliver lifesaving organs for patients without recourse to long-term immunosuppression.

Methods

Animals. All experiments were performed according to guidelines established by the Stanford University Administrative Panel on Laboratory Animal Care. AKR×C57BL/6 F1 donors were crossed and bred in house. CB6F1 and DBA1/J recipients were purchased from the Jackson Laboratory. DBA1/J pregnant females were purchased from Taconic Biosciences for ear heart grafts.

Antibodies. Anti-CD47 (mIAP410), anti-c-KIT (ACK2), anti-CD122 (Tm-β1), anti-CD40L (MR1), anti-CD4 (GK1.5), and anti-CD8 (YTS169.4) were purchased from BioXCell. Anti-CD47 was given intraperitoneally as a 100 g dose on Day −8 and then as a 500 g dose for subsequent injections throughout the conditioning process. Retro-orbital anti-c-KIT and intraperitoneal anti-CD40L were both given as one time 500 g boluses. Anti-CD122 was given intraperitoneally as a 250 μg dose while anti-CD4 and anti-CD8 were given as 100 μg intraperitoneal doses. Mice receiving anti-c-KIT antibody were given 400 g of diphenhydramine intraperitoneally 15 minutes prior to injection. Anti-CD25 (PC-61.5.3) was purchased from BioXCell and given as a one-time 100 g intraperitoneal injection.

Graft Preparation and Transplantation. Whole bone marrow was extracted from donor mice tibia, femurs, hips, and spine. Bones were crushed, filtered, and subsequently underwent red blood cell (RBC) lysis. For c-Kit enriched transplants, RBC lysed whole bone marrow were bound to Miltenyi CD117 MicroBeads as per the manufacturer's instructions and collected after magnetic separation. For LSK cell transplants, RBC lysed whole bone marrow were bound to the Miltenyi Lineage Cell Depletion Kit cocktail as per the manufacturer's instructions. Flow through from the magnetic separation columns was collected and stained in PBS with 2% FBS with optimal concentrations of the following antibodies: CD3 PE (17A2), CD4 PE (GK1.5), CD5 PE (53-7.3), CD8a PE (53-6.7), B220 PE (RA3-6B2), Gr-1 PE (RB6-8C5), Mac-1 PE (M1/70), Ter119 PE (TER119), SCA1 Pe-Cy7 (D7), and CD117 APC (2B8). Propidium iodide was added as a viability stain just prior to sorting on a BD Aria. All cells for transplant were resuspended at the desired concentration in PBS with 2% FBS. Irradiation control mice were lethally irradiated with two doses of 6.5Gy prior to transplantation. All mice were anesthetized using isoflurane and then transplanted with 100 μL of cell suspension via retroorbital injection.

Peripheral Blood Chimerism. Mice were periodically bled via retroorbital bleeding into EDTA coated tubes. Blood was then incubated in 1% dextran with 5 mM EDTA at 37C for 1 hour. The supernatant from each tube was extracted, lysed and then stained with optimal concentrations of the following antibodies: CD3 APC (17A2), CD19 PE-Cy7 (ebio103), Gr-1 BV421 (RB6-8C5), Mac-1 APC-Cy7 (M1/70), CD45.1 FITC (A20), and CD45.2 PE (104). Samples were analyzed on a BD Fortessa and donor versus host chimerism was distinguished based on CD45 allelic differences.

Ear-Heart Graft. Neonatal mice were euthanized 1-2 days after birth and their hearts were harvested. Recipient mice were prepared by making a small incision on the dorsal side of their ear near the skull. Afterward, using a trocar, a pouch was created by tunneling from the incision site to the tip of the pinna. Neonatal hearts were delivered at the distal end of the pouch with the trocar. The tunnel was closed by gently pushing the lifted skin back to the dermis. Heart viability was monitored for beating by visualizing the graft through a dissecting microscope.

REFERENCES

Lv et al. Autoimmune hematological diseases following haploidentical donor hematopoietic stem cell Transplant compared with matched sibling and unrelated donor. Oncotarget. 2017; 8(16):26505-26514.

Gandy and Weissman. Tolerance of allogeneic heart grafts in mice simultaneously reconstituted with purified allogeneic hematopoietic stem cells. Transplantation. 1998; 65(3):295-304.

Shizuru et al. Purified hematopoietic stem cell grafts induce tolerance to alloantigens and can mediate positive and negative T cell selection. Proc Natl Acad Sci USA. 2000; 97(17):9555-60.

Passweg et al. Use of haploidentical stem cell transplantation continues to increase: the 2015 European Society for Blood and Marrow Transplant activity survey report. Bone Marrow Transplant. 2017; 52(6):811-817.

Gragert et al. HLA match likelihoods for hematopoietic stem-cell grafts in the U.S. registry. N Engl J Med. 2014; 371(4):339-48.

Cobbold S P, Martin G, Qin S, Waldmann H. Monoclonal antibodies to promote marrow engraftment and tissue graft tolerance. Nature. 1986; 323(6084):164-6.

Palchaudhuri et al. Non-genotoxic conditioning for hematopoietic stem cell transplantation using a hematopoietic-cell-specific internalizing immunotoxin. Nat Biotechnol. 2016; 34(7):738-45.

Czechowicz et al. Efficient transplantation via antibody-based clearance of hematopoietic stem cell niches. Science. 2007; 318(5854):1296-9.

Chhabra et al. Hematopoietic stem cell transplantation in immunocompetent hosts without radiation or chemotherapy. Sci Transl Med. 2016; 8(351):351ra105.

Ruggeri et al. Effectiveness of donor natural killer cell alloreactivity in mismatched hematopoietic transplants. Science. 2002; 295(5562):2097-100.

Durham et al. Cutting edge: administration of anti-CD40 ligand and donor bone marrow leads to hemopoietic chimerism and donor-specific tolerance without cytoreductive conditioning. J Immunol. 2000; 165(1):1-4.

Wekerle et al. Allogeneic bone marrow transplantation with co-stimulatory blockade induces macrochimerism and tolerance without cytoreductive host treatment. Nat Med. 2000; 6(4):464-9.

Markees et al. Prolonged survival of mouse skin allografts in recipients treated with donor splenocytes and antibody to CD40 ligand. Transplantation. 1997; 64(2):329-35.

Shizuru et al. Transplantation of purified hematopoietic stem cells: requirements for overcoming the barriers of allogeneic engraftment. Biol Blood Marrow Transplant. 1996; 2(1):3-14.

Negrin et al. Transplantation of highly purified CD34+Thy-1+ hematopoietic stem cells in patients with metastatic breast cancer. Biol Blood Marrow Transplant. 2000; 6(3): 262-71.

Tsao et al. Purified hematopoietic stem cell allografts reconstitute immunity superior to bone marrow. Proc Natl Acad Sci USA. 2009; 106(9):3288-93.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of providing for engraftment of HLA-mismatched hematopoietic stem cells in an immunocompetent human subject, the method comprising a conditioning regimen of:
   contacting said subject concomitantly with (i) an antibody that specifically binds to CD117 and (ii) an agent that blocks interaction between CD47 and SIRPα; in a dose effective to ablate targeted endogenous hematopoietic stem cells from bone marrow of said subject;
   introducing a cellular composition comprising exogenous allogeneic hematopoietic stem cells mismatched at one or more major MHC loci to said subject, following a wash-out period of time sufficient to reduce the serum level of (i) and (ii) to non-toxic levels in the subject, the cellular composition comprising: exogenous hematopoietic stem cells mismatched at one or more major MHC loci; and
   concomitantly contacting said subject with (iii) an agent that induces transient immunosuppression, wherein the agent is an anti-CD40L antibody; and
   contacting the subject with (iv) an agent the depletes NK cells, wherein the agent (iv) is administered prior to or concurrently with the exogenous stem cells;
   wherein the exogenous stem cells engraft in the absence of myeloablative conditioning.

2. The method of claim 1, wherein the agent that blocks interaction between CD47 and SIRPα is selected from: a soluble SIRPα polypeptide; an antibody specific for CD47, an antibody specific for SIRPα, and a soluble CD47 polypeptide.

3. The method of claim 1, wherein the subject is haploidentical relative to the exogenous stem cells.

4. The method of claim 1, wherein an agent (iv) that selectively depletes NK cells is selected from an antibody specific for one or more of CD122 and CD56.

5. The method of claim 1, wherein the agent (iv) is an antibody selected from an antibody specific for CD2, CD52, CD45; or anti-thymocyte globulin (ATG).

6. The method of claim 1, wherein an agent (iv) further comprises an agent that selectively depletes T cells, selected from an antibody specific for one or more of CD3, CD4, and CD8.

7. The method of claim 5, wherein the cellular composition comprises at least 50% hematopoietic stem cells selected for $CD34^+$ expression from bone marrow, cord blood, or peripheral blood.

8. The method of claim 6, wherein the cellular composition comprises at least 50% hematopoietic stem cells selected for $CD34^+$ expression from bone marrow, cord blood, or peripheral blood.

9. The method of claim 5, wherein the cellular composition comprises hematopoietic stem cells derived from pluripotent cells in vitro.

10. The method of claim 5, wherein the cellular composition comprises at least $10^5$ $CD34^+$ cells/kg of recipient body weight.

* * * * *